(12) United States Patent
Liew et al.

(10) Patent No.: US 9,347,076 B2
(45) Date of Patent: May 24, 2016

(54) RECOMBINANT MICROORGANISMS THAT MAKE BIODIESEL

(71) Applicant: LanzaTech New Zealand Limited, Auckland (NZ)

(72) Inventors: FungMin Liew, Auckland (NZ); Michael Koepke, Auckland (NZ)

(73) Assignee: LANZATECH NEW ZEALAND LIMITED, Auckland (NZ)

( * ) Notice: Subject to any disclaimer, the term of this patent is extended or adjusted under 35 U.S.C. 154(b) by 239 days.

(21) Appl. No.: 13/923,352

(22) Filed: Jun. 20, 2013

(65) Prior Publication Data

US 2013/0344547 A1 Dec. 26, 2013

Related U.S. Application Data

(60) Provisional application No. 61/662,467, filed on Jun. 21, 2012.

(51) Int. Cl.
| | |
|---|---|
| *C12N 1/21* | (2006.01) |
| *C12P 7/64* | (2006.01) |
| *C12N 9/10* | (2006.01) |
| *C10L 1/02* | (2006.01) |

(52) U.S. Cl.
CPC ............ *C12P 7/649* (2013.01); *C10L 1/026* (2013.01); *C12N 9/1029* (2013.01); *C12Y 203/0102* (2013.01); *C12Y 203/01075* (2013.01); *Y02E 50/13* (2013.01); *Y02P 20/52* (2015.11)

(58) Field of Classification Search
CPC ....... C10L 1/026; C12N 9/1029; C12P 7/649; C12Y 203/0102; C12Y 203/01075; Y02E 50/13
See application file for complete search history.

(56) References Cited

U.S. PATENT DOCUMENTS

| | | | |
|---|---|---|---|
| 5,173,429 | A | 12/1992 | Gaddy et al. |
| 5,593,886 | A | 1/1997 | Gaddy et al. |
| 6,368,819 | B1 | 4/2002 | Gaddy et al. |
| 2011/0229947 | A1 | 9/2011 | Zahn et al. |
| 2012/0115195 | A1 | 5/2012 | Keasling et al. |

FOREIGN PATENT DOCUMENTS

| | | |
|---|---|---|
| WO | WO02-08438 | 1/2002 |
| WO | WO2008-028055 | 3/2008 |
| WO | WO2009-064200 | 5/2009 |
| WO | WO2012-115527 | 8/2012 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Gustafsson et al., Trends in Biotechnology 22(7):346-353, 2004.*
Stoveken et al., Journal of Bacteriology 187(4):1369-1376, 2005.*
Munasinghe et al., Bioresource Technology 101:5013-5022, 2010.*
Lepage et al., Journal of General Microbiology 133:103-110, 1987.*
Abrini, J., Naveau, H., & Nyns, E. J. *Clostridium autoethanogenum*, sp. nov., an anaerobic bacterium that produces ethanol from carbon monoxide. Archives of microbiology, 161(4), 345-351(1994).
Collins, M. D., Lawson, P. A., Willems, A., Cordoba, J. J., Fernandez-Garayzabal, J., Garcia, P., Cai, J., et al. The phylogeny of the genus *Clostridium*: proposal of five new genera and eleven new species combinations. International journal of systematic bacteriology, 44(4), 812-26(1994).
Herbert, M., O'Keeffe, T. a., Purdy, D., Elmore, M., & Minton, N. P. Gene transfer into Clostridium difficile CD630 and characterisation of its methylase genes. FEMS Microbiology Letters, 229(1), 103-110(2003).
Jennert, K. C., Tardif, C., Young, D. I., & Young, M. Gene transfer to Clostridium cellulolyticum ATCC 35319. Microbiology (Reading, England), 146 Pt 12, 3071-80(2000).
Kita, A., Iwasaki, Y., Sakai, S., Okuto, S., Takaoka, K., Suzuki, T., Yano, S., et al. Development of genetic transformation and heterologous expression system in carboxydotrophic thermophilic acetogen Moorella thermoacetica. Journal of Bioscience and Bioengineering, vol. 115 (4) pp. 347-352 (2013).
Köpke, M., Held, C., Hujer, S., Liesegang, H., Wiezer, A., Wollherr, A., Ehrenreich, A., et al. Clostridium ljungdahlii represents a microbial production platform based on syngas. Proceedings of the National Academy of Sciences of the United States of America, 107(29)(2010).
Köpke, M., Mihalcea, C., Liew, F., Tizard, J. H., Ali, M. S., Conolly, J. J., Al-Sinawi, B., et al. 2,3-Butanediol Production by Acetogenic Bacteria, an Alternative Route to Chemical Synthesis, Using Industrial Waste Gas. Applied and environmental microbiology, 77(15), 5467-75(2011).
Leang, C., Ueki, T., Nevin, K. P., & Lovley, D. R. A Genetic System for Clostridium Ijungdahlii: A Chassis for Autotrophic Production of Biocommodities and a Model Homoacetogen. Applied and environmental microbiology, (Nov.)(2012).
Mermelstein, L. D., Welker, N. E., Bennett, G. N., & Papoutsakis, E. T. Expression of cloned homologous fermentative genes in Clostridium acetobutylicum ATCC 824. Bio/technology (Nature Publishing Company), 10(2), 190-195(1992).
Perez, J. M., Richter, H., Loftus, S. E., & Angenent, L. T. Biocatalytic reduction of short-chain carboxylic acids into their corresponding alcohols with syngas fermentation. Biotechnology and bioengineering, 1-30(2012).

(Continued)

*Primary Examiner* — Delia Ramirez
(74) *Attorney, Agent, or Firm* — Andrea E. Schoen

(57) ABSTRACT

A carboxydotrophic acetogenic recombinant microorganism is modified so that it produces biodiesel and optionally one or more other products by fermentation of a substrate comprising CO. Biodiesel is produced by microbial fermentation of a substrate comprising CO. The recombinant microorganism is modified to express one or more exogenous enzymes in the biodiesel biosynthesis pathway not present in a parental microorganism from which the recombinant microorganism is derived. The one or more enzymes comprise a nonspecific acyltransferase.

12 Claims, 3 Drawing Sheets

(56) References Cited

OTHER PUBLICATIONS

Strätz, M., Sauer, U., Kuhn, a, & Dürre, P. Plasmid Transfer into the Homoacetogen Acetobacterium woodii by Electroporation and Conjugation. Applied and environmental microbiology, 60(3), 1033-7(1994).

Tanner, R. S., Miller, L. M., & Yang, D. *Clostridium Ijungdahlii* sp. nov., an acetogenic species in clostridial rRNA homology group I. International journal of systematic bacteriology, 43(2), 232(1993).

Tyurin, Michael, & Kiriukhin, M. Electrofusion of cells of Acetogen *Clostridium* sp. MT 351 with erm (B) or cat in the chromosome. Journal of Biotech, 1-12(2012).

Tyurin, MV, Desai, S., & Lynd, L. Electrotransformation of Clostridium thermocellum. Applied and environmental mictrobiology 70(2), 883-890(2004).

Williams, D. R., Young, D. I., & Young, M. Conjugative plasmid transfer from *Escherichia coli* to Clostridium acetobutylicum. Journal of general microbiology, 136(5), 819-26(1990).

Tirado-Acevedo O. Production of Bioethanol from Synthesis Gas Using Clostridium Ijungdahlii. PhD thesis, North Carolina State University, 2010.

Murray, N.E. et al. (2000) Microbial. Molec. Biol. Rev. 64, 412.

Köpke & Dürre, Biochemical production of biobutanol, In: Handbook of biofuels production: processes and technologies (Eds.: Luque, Campelo & Clark), Woodhead Publishing Ltd, Camebridge, UK: 221-257 (2011).

Ismail et al., J. Bacteriol, 1993, 175: 5079-5105.

Kalscheuer, Rainer et al., "Microdiesel: *Escherichia coli* engineered for fuel production", Microbiology, 2006, vol. 152 pp. 2529-2536.

Kopke, Michael et al.. "Clostridium Ijungdahlii represents a microbial production platform based on syngas", PNAS, Jul. 10, 2010, vol. 107, No. 29, pp. 13087-13092.

Kim, Ok Bin et al., "Biotransformation of glycidol by the unspecific wax ester synthase/acyl-coa:diacylglycerol acyltransferase of acinetobacter baylyi ADP1", European Journal of Lipid Science and Technology, 2009, vol. 111, pp. 972-978.

Yan, Yajun et al., "Engineering metabolic systems for production of advanced fuels", Journal of Industrial Microbiology and Biotechnology, 2009, vol. 36, pp. 471-479.

\* cited by examiner

SEQUENCE LISTING

<160> NUMBER OF SEQ ID NOS: 18

<210> SEQ ID NO 1
<211> LENGTH: 1383
<212> TYPE: DNA
<213> ORGANISM: Artificial Sequence
<220> FEATURE:
<223> OTHER INFORMATION: codon optimized acyltransferase gene

<400> SEQUENCE: 1

```
atgagacctt tacaccctat tgattttatt tttcttagtc ttgaaaagag acaacaacct      60
atgcatgttg gaggattatt tttatttcaa atacctgata atgcaccaga tactttata     120 caggatcttg taaatgatat taggatatca aaaagtattc ctgtaccacc atttaataat     180
aagcttaatg gattattttg ggatgaagat gaagaatttg atcttgatca tcattttaga     240
catattgcac ttcctcatcc tggtagaata agagaacttc ttatttatat atctcaggaa     300
catagtacac ttttagatag agctaaacct ttatggactt gcaatattat agaaggaata     360
gaaggaaata gatttgcaat gtattttaag attcaccatg caatggtaga tggagtagca     420
ggaatgagat taattgaaaa atcactttct cacgatgtaa ctgaaaaatc aatagtacct     480
ccttggtgtg tagaaggtaa gagagcaaaa agacttagag aacctaaaac aggtaaaata     540
aagaaaataa tgtcaggaat aaagagtcaa ttacaagcta ctccaactgt aatacaggaa     600
cttagtcaaa ctgtttttaa ggatattggt agaaatccag atcatgtaag ttcttttcag     660
gctccttgtt caatttaaa tcagagagtt tcatcatcaa gaaggtttgc agcacaatct     720
tttgatttag ataggtttag gaatatagca aagagtctta atgtaactat aaatgatgtt     780
```

-continued

```
gtacttgcag tttgttctgg tgcacttaga gcttatttaa tgtctcacaa ttcattacct      840
agtaagccat taattgcaat ggttcctgca tctataagaa atgatgatag tgatgtttct      900
aataggatta caatgatact tgctaatctt gctacacaca aagatgatcc attacaaaga     960
cttgaaataa taaggagaag tgttcaaaat tctaaacaaa ggtttaaaag gatgactagt    1020
gatcagattc ttaattattc agctgtagtt tatggaccag caggtcttaa tattatatct    1080
ggtatgatgc caaaaaggca ggcttttaat ttagttatta gtaatgttcc aggtccaaga    1140
gaacctcttt attggaatgg agctaagctt gatgctcttt atccagcttc tatagtactt    1200
gatggtcagg cacttaatat aacaatgaca tcatatcttg ataagcttga agttggactt    1260
attgcttgta ggaatgctct tccaaggatg cagaatttac ttacacatct tgaagaagaa    1320
atacaacttt tgaaggtgt aatagctaag caggaagata ttaaaactgc aaattaagaa     1380
ttc                                                                    1383

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide Ppta-ack-NotI-F

<400> SEQUENCE: 2
gagcggccgc aatatgatat ttatgtcc                                         28

<210> SEQ ID NO 3
<211> LENGTH: 28
<212> TYPE: DNA
<213> ORGANISM: Artificial Sequence
<220> FEATURE:
<223> OTHER INFORMATION: Oligonucleotide Ppta-ack-NdeI-R

<400> SEQUENCE: 3
ttccatatgt tcatgttca tttcctcc                                          28

<210> SEQ ID NO 4
<211> LENGTH: 419
<212> TYPE: DNA
<213> ORGANISM: Clostridium autoethanogenum

<400> SEQUENCE: 4
agaaattttc ctttctaaaa tatttattc catgtcaaga actctgttta tttcattaaa       60
gaactataag tacaaagtat aaggcatttg aaaaaatagg ctagtatatt gattgattat    120
ttattttaaa atgcctaagt gaaatatata catattataa caataaaata agtattagtg    180
taggattttt aaatagagta tctattttca gattaaattt ttgattattt gatttacatt    240
atataatatt gagtaaagta ttgactagca aaattttttg atactttaat ttgtgaaatt    300
tcttatcaaa agttatattt tgaataatt tttattgaaa aatacaacta aaaggatta     360 tagtataagt gtgtgtaatt ttgtgttaaa tttaagggga ggaaatgaac atgaaattg      419

<210> SEQ ID NO 5
<211> LENGTH: 4912
<212> TYPE: DNA
<213> ORGANISM: Artificial Sequence
<220> FEATURE:
<223> OTHER INFORMATION: plasmid pMTL85245-atf

<400> SEQUENCE: 5
aaactccttt tgataatct catgaccaaa atcccttaac gtgagttttc gttccactga      60
```

-continued

```
gcgtcagacc ccgtagaaaa gatcaaagga tcttcttgag atccttttt tctgcgcgta      120 atctgctgct tgcaaacaaa aaaccaccg ctaccagcgg tggtttgttt gccggatcaa      180
gagctaccaa ctcttttcc gaaggtaact ggcttcagca gagcgcagat accaaatact      240
gttcttctag tgtagccgta gttaggccac cacttcaaga actctgtagc accgcctaca     300
tacctcgctc tgctaatcct gttaccagtg gctgctgcca gtggcgataa gtcgtgtctt    360
accgggttgg actcaagacg atagttaccg gataaggcgc agcggtcggg ctgaacgggg    420
ggttcgtgca cacagcccag cttggagcga acgacctaca ccgaactgag atacctacag    480
cgtgagctat gagaaagcgc cacgcttccc gaagggagaa aggcggacag gtatccgta     540 agcggcaggg tcggaacagg agagcgcacg agggagcttc caggggggaaa cgcctggtat   600 ctttatagtc ctgtcgggtt tcgccacctc tgacttgagc gtcgatttt gtgatgctcg     660 tcaggggggc ggagcctatg gaaaaacgcc agcaacgcgg ccttttacg gttcctggcc     720 ttttgctggc cttttgctca catgttcttt cctgcgttat ccctgattc tgtggataac     780 cgtattaccg cctttgagtg agctgatacc gctcgccgca gccgaacgac cgagcgcagc    840
gagtcagtga gcgaggaagc ggaagagcgc ccaatacgca gggcccctg caggataaaa     900 aaattgtaga taaattttat aaaatagttt tatctacaat ttttttatca ggaaacagct    960
atgaccgcgg ccgcaatatg atatttatgt ccattgtgaa agggattata ttcaactatt    1020
attccagtta cgttcataga aattttcctt tctaaaatat tttattccat gtcaagaact   1080
ctgtttattt cattaaagaa ctataagtac aaagtataag gcatttgaaa aaataggcta   1140
gtatattgat tgattattta ttttaaaatg cctaagtgaa atatatacat attataacaa   1200
taaaataagt attagtgtag gattttaaa tagagtatct attttcagat taaatttttg    1260
attatttgat ttacattata taatattgag taaagtattg actagcaaaa ttttttgata   1320
ctttaatttg tgaaatttct tatcaaaagt tatattttg ataattttt attgaaaaat     1380 acaactaaaa aggattatag tataagtgtg tgtaattttg tgttaaattt aagggagga    1440 aatgaacatg aaacatatga gacctttaca ccctattgat tttatttttc ttagtcttga   1500
aaagagacaa caacctatgc atgttggagg attatttta tttcaaatac ctgataatgc    1560
accagatact tttatacagg atcttgtaaa tgatattagg atatcaaaaa gtattcctgt   1620
accaccattt aataataagc ttaatggatt atttttgggat gaagatgaag aatttgatct   1680
tgatcatcat tttagacata ttgcacttcc tcatcctggt agaataagag aacttcttat   1740
ttatatatct caggaacata gtacactttt agatagagct aaaccttat ggacttgcaa    1800 tattatagaa ggaatagaag gaaatagatt tgcaatgtat tttaagattc accatgcaat   1860
ggtagatgga gtagcaggaa tgagattaat tgaaaaatca ctttctcacg atgtaactga   1920
aaaatcaata gtacctcctt ggtgtgtaga aggtaagaga gcaaaaagac ttagagaacc   1980
taaaacaggt aaaataaaga aaataatgtc aggaataaag agtcaattac aagctactcc   2040
aactgtaata caggaactta gtcaaactgt ttttaaggat attggtagaa atccagatca   2100
tgtaagttct tttcaggctc cttgttcaat tttaaatcag agagttcat catcaagaag    2160 gtttgcagca caatcttttg atttagatag gtttaggaat atagcaaaga gtcttaatgt    2220
aactataaat gatgttgtac ttgcagtttg ttctggtgca cttagagctt atttaatgtc    2280
tcacaattca ttacctagta agccattaat tgcaatggtt cctgcatcta taagaaatga    2340
tgatagtgat gtttctaata ggattacaat gatacttgct aatcttgcta cacacaaaga    2400
```

-continued

```
tgatccatta caaagacttg aaataataag gagaagtgtt caaaattcta aacaaaggtt    2460
taaaaggatg actagtgatc agattcttaa ttattcagct gtagtttatg gaccagcagg    2520
tcttaatatt atatctggta tgatgccaaa aaggcaggct tttaatttag ttattagtaa    2580
tgttccaggt ccaagagaac ctctttattg gaatggagct aagcttgatg ctctttatcc    2640
agcttctata gtacttgatg gtcaggcact aatataaca atgacatcat atcttgataa    2700
gcttgaagtt ggacttattg cttgtaggaa tgctcttcca aggatgcaga atttacttac    2760
acatcttgaa gaagaaatac aacttttttga aggtgtaata gctaagcagg aagatattaa    2820
aactgcaaat taagaattcg agctcggtac ccggggatcc tctagagtcg acgtcacgcg    2880
tccatggaga tctcgaggcc tgcagacatg caagcttggc actggccgtc gttttacaac    2940
gtcgtgactg ggaaaaccct ggcgttaccc aacttaatcg ccttgcagca catcccctt     3000 tcgccagctg gcgtaatagc gaagaggccc gcaccgatcg cccttcccaa cagttgcgca    3060
gcctgaatgg cgaatggcgc tagcataaaa ataagaagcc tgcatttgca ggcttcttat    3120
ttttatggcg cgccgcattc acttcttttc tatataaata tgagcgaagc gaataagcgt    3180
cggaaaagca gcaaaagtt tccttttttgc tgttggagca tgggggttca ggggggtgcag   3240 tatctgacgt caatgccgag cgaaagcgag ccgaagggta gcatttacgt tagataaccc    3300
cctgatatgc tccgacgctt tatatagaaa agaagattca actaggtaaa atcttaatat    3360
aggttgagat gataaggttt ataaggaatt tgtttgttct aattttcac tcattttgtt     3420 ctaatttctt ttaacaaatg ttcttttttt tttagaacag ttatgatata gttagaatag    3480
tttaaaataa ggagtgagaa aaagatgaaa gaaagatatg gaacagtcta taaggctct     3540 cagaggctca tagacgaaga aagtggagaa gtcatagagg tagacaagtt ataccgtaaa    3600
caaacgtctg gtaacttcgt aaaggcatat atagtgcaat taataagtat gttagatatg    3660
attggcggaa aaaaacttaa aatcgttaac tatatcctag ataatgtcca cttaagtaac    3720
aatacaatga tagctacaac aagagaaata gcaaaagcta caggaacaag tctacaaaca    3780
gtaataacaa cacttaaaat cttagaagaa ggaaatatta taaaaagaaa aactggagta    3840
ttaatgttaa acccctgaact actaatgaga ggcgacgacc aaaaacaaaa atacctctta    3900
ctcgaatttg ggaactttga gcaagaggca aatgaaatag attgacctcc caataacacc    3960
acgtagttat tgggaggtca atctatgaaa tgcgattaag ggccggccga agcaaactta    4020
agagtgtgtt gatagtgcag tatcttaaaa ttttgtataa taggaattga agttaaatta    4080
gatgctaaaa atttgtaatt aagaaggagt gattacatga acaaaaatat aaaatattct    4140
caaaactttt taacgagtga aaaagtactc aaccaaataa taaaacaatt gaatttaaaa    4200
gaaaccgata ccgtttacga aattggaaca ggtaaagggc atttaacgac gaaactggct    4260
aaaataagta aacaggtaac gtctattgaa ttagacagtc atctattcaa cttatcgtca    4320
gaaaaattaa aactgaatac tcgtgtcact ttaattcacc aagatattct acagtttcaa    4380
ttccctaaca aacagaggta taaaattgtt gggagtattc cttaccatt aagcacacaa     4440 attattaaaa aagtggtttt tgaaagccat gcgtctgaca tctatctgat tgttgaagaa    4500
ggattctaca agcgtacctt ggatattcac cgaacactag gttgctctt gcacactcaa     4560 gtctcgattc agcaattgct taagctgcca gcggaatgct ttcatcctaa accaaaagta    4620
aacagtgtct aataaaaact tacccgccat accacagatg ttccagataa atattggaag    4680
ctatatacgt acttttgttc aaaatgggtc aatcgagaat atcgtcaact gtttactaaa    4740
aatcagtttc atcaagcaat gaaacacgcc aaagtaaaca atttaagtac cgttacttat    4800
```

```
gagcaagtat tgtctatttt taatagttat ctattattta acgggaggaa ataattctat    4860
gagtcgcttt tgtaaatttg gaaagttaca cgttactaaa gggaatgtgt tt            4912
```

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide Atf-F1

<400> SEQUENCE: 6

```
agacaacaac ctatgcatgt tggagga                                        27
```

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide Atf-R1

<400> SEQUENCE: 7

```
ggggatgtgc tgcaaggcga                                                20
```

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide Atf-F2

<400> SEQUENCE: 8

```
catcatcaag aaggtttgca gcacaat                                        27
```

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide Atf-R2

<400> SEQUENCE: 9

```
agaggttctc ttggacctgg aacat                                          25
```

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide Atf-F3

<400> SEQUENCE: 10

```
tcggtacccg gggatcctct a                                              21
```

<210> SEQ ID NO 11
<211> LENGTH: 27
<212> TYPE: DNA
<213> ORGANISM: Artificial Sequence
<220> FEATURE:
<223> OTHER INFORMATION: Oligonucleotide Atf-R3

<400> SEQUENCE: 11

```
cattcctgct actccatcta ccattgc                                        27
```

<210> SEQ ID NO 12

```
<211> LENGTH: 601
<212> TYPE: PRT
<213> ORGANISM: Artificial Sequence
<220> FEATURE:
<223> OTHER INFORMATION: designed methyltransferase

<400> SEQUENCE: 12
```

Met Phe Pro Cys Asn Ala Tyr Ile Glu Tyr Gly Asp Lys Asn Met Asn
1               5                   10                  15

Ser Phe Ile Glu Asp Val Glu Gln Ile Tyr Asn Phe Ile Lys Lys Asn
            20                  25                  30

Ile Asp Val Glu Glu Lys Met His Phe Ile Glu Thr Tyr Lys Gln Lys
        35                  40                  45

Ser Asn Met Lys Lys Glu Ile Ser Phe Ser Glu Glu Tyr Tyr Lys Gln
    50                  55                  60

Lys Ile Met Asn Gly Lys Asn Gly Val Val Tyr Thr Pro Pro Glu Met
65                  70                  75                  80

Ala Ala Phe Met Val Lys Asn Leu Ile Asn Val Asn Asp Val Ile Gly
                85                  90                  95

Asn Pro Phe Ile Lys Ile Ile Asp Pro Ser Cys Gly Ser Gly Asn Leu
            100                 105                 110

Ile Cys Lys Cys Phe Leu Tyr Leu Asn Arg Ile Phe Ile Lys Asn Ile
        115                 120                 125

Glu Val Ile Asn Ser Lys Asn Asn Leu Asn Leu Lys Leu Glu Asp Ile
    130                 135                 140

Ser Tyr His Ile Val Arg Asn Asn Leu Phe Gly Phe Asp Ile Asp Glu
145                 150                 155                 160

Thr Ala Ile Lys Val Leu Lys Ile Asp Leu Phe Leu Ile Ser Asn Gln
                165                 170                 175

Phe Ser Glu Lys Asn Phe Gln Val Lys Asp Phe Leu Val Glu Asn Ile
            180                 185                 190

Asp Arg Lys Tyr Asp Val Phe Ile Gly Asn Pro Pro Tyr Ile Gly His
        195                 200                 205

Lys Ser Val Asp Ser Ser Tyr Ser Tyr Val Leu Arg Lys Ile Tyr Gly
    210                 215                 220

Ser Ile Tyr Arg Asp Lys Gly Asp Ile Ser Tyr Cys Phe Phe Gln Lys
225                 230                 235                 240

Ser Leu Lys Cys Leu Lys Glu Gly Gly Lys Leu Val Phe Val Thr Ser
                245                 250                 255

Arg Tyr Phe Cys Glu Ser Cys Ser Gly Lys Glu Leu Arg Lys Phe Leu
            260                 265                 270

Ile Glu Asn Thr Ser Ile Tyr Lys Ile Ile Asp Phe Tyr Gly Ile Arg
        275                 280                 285

Pro Phe Lys Arg Val Gly Ile Asp Pro Met Ile Ile Phe Leu Val Arg
    290                 295                 300

Thr Lys Asn Trp Asn Asn Asn Ile Glu Ile Arg Pro Asn Lys Ile
305                 310                 315                 320

Glu Lys Asn Glu Lys Asn Lys Phe Leu Asp Ser Leu Phe Leu Asp Lys
                325                 330                 335

Ser Glu Lys Cys Lys Lys Phe Ser Ile Ser Gln Lys Ser Ile Asn Asn
            340                 345                 350

Asp Gly Trp Val Phe Val Asp Glu Val Glu Lys Asn Ile Ile Asp Lys
        355                 360                 365

Ile Lys Glu Lys Ser Lys Phe Ile Leu Lys Asp Ile Cys His Ser Cys
    370                 375                 380

Gln Gly Ile Ile Thr Gly Cys Asp Arg Ala Phe Ile Val Asp Arg Asp
385                 390                 395                 400

Ile Ile Asn Ser Arg Lys Ile Glu Leu Arg Leu Ile Lys Pro Trp Ile
            405                 410                 415

Lys Ser Ser His Ile Arg Lys Asn Glu Val Ile Lys Gly Glu Lys Phe
        420                 425                 430

Ile Ile Tyr Ser Asn Leu Ile Glu Asn Glu Thr Glu Cys Pro Asn Ala
            435                 440                 445

Ile Lys Tyr Ile Glu Gln Tyr Lys Lys Arg Leu Met Glu Arg Arg Glu
        450                 455                 460

Cys Lys Lys Gly Thr Arg Lys Trp Tyr Glu Leu Gln Trp Gly Arg Lys
465                 470                 475                 480

Pro Glu Ile Phe Glu Glu Lys Lys Ile Val Phe Pro Tyr Lys Ser Cys
                485                 490                 495

Asp Asn Arg Phe Ala Leu Asp Lys Gly Ser Tyr Phe Ser Ala Asp Ile
            500                 505                 510

Tyr Ser Leu Val Leu Lys Lys Asn Val Pro Phe Thr Tyr Glu Ile Leu
        515                 520                 525

Leu Asn Ile Leu Asn Ser Pro Leu Tyr Glu Phe Tyr Phe Lys Thr Phe
    530                 535                 540

Ala Lys Lys Leu Gly Glu Asn Leu Tyr Glu Tyr Tyr Pro Asn Asn Leu
545                 550                 555                 560

Met Lys Leu Cys Ile Pro Ser Ile Asp Phe Gly Gly Glu Asn Asn Ile
                565                 570                 575

Glu Lys Lys Leu Tyr Asp Phe Phe Gly Leu Thr Asp Lys Glu Ile Glu
            580                 585                 590

Ile Val Glu Lys Ile Lys Asp Asn Cys
        595                 600

<210> SEQ ID NO 13
<211> LENGTH: 1940
<212> TYPE: DNA
<213> ORGANISM: Artificial Sequence
<220> FEATURE:
<223> OTHER INFORMATION: designed methyltransferase gene fused with an
      inducible lac Promoter

<400> SEQUENCE: 13
gcggccgcgc aacgcaatta atgtgagtta gctcactcat taggcacccc aggctttaca    60
ctttatgctt ccggctcgta tgttgtgtgg aattgtgagc ggataacaat ttcacacagg   120
aaacacatat gtttccgtgc aatgcctata tcgaatatgg tgataaaaat atgaacagct   180
ttatcgaaga tgtggaacag atctacaact tcattaaaaa gaacattgat gtggaagaaa   240
agatgcattt cattgaaacc tataaacaga aaagcaacat gaagaaagag attagcttta   300
gcgaagaata ctataaacag aagattatga cgcaaaaaa tggcgttgtg tacaccccgc   360
cggaaatggc ggccttttatg gttaaaaatc tgatcaacgt taacgatgtt attggcaatc   420
cgtttattaa atcattgac cgagctgcg gtagcggcaa tctgatttgc aaatgttttc    480
tgtatctgaa tcgcatcttt attaagaaca ttgaggtgat taacagcaaa ataacctga    540 atctgaaact ggaagacatc agctaccaca tcgttcgcaa caatctgttt ggcttcgata    600
ttgacgaaac cgcgatcaaa gtgctgaaaa ttgatctgtt tctgatcagc aaccaattta    660
gcgagaaaaa tttccaggtt aaagactttc tggtggaaaa tattgatcgc aaatatgacg    720
tgttcattgg taatccgccg tatatcggtc acaaaagcgt ggacagcagc tacagctacg    780

-continued

```
tgctgcgcaa aatctacggc agcatctacc gcgacaaagg cgatatcagc tattgtttct    840
ttcagaagag cctgaaatgt ctgaaggaag gtggcaaact ggtgtttgtg accagccgct    900
acttctgcga gagctgcagc ggtaaagaac tgcgtaaatt cctgatcgaa aacacgagca    960
tttacaagat cattgatttt tacggcatcc gcccgttcaa acgcgtgggt atcgatccga   1020
tgattatttt tctggttcgt acgaagaact ggaacaataa cattgaaatt attcgcccga   1080
acaagattga aagaacgaa aagaacaaat tcctggatag cctgttcctg acaaaagcg    1140
aaaagtgtaa aaagtttagc attagccaga aaagcattaa taacgatggc tgggttttcg   1200
tggacgaagt ggagaaaaac attatcgaca aaatcaaaga gaaaagcaag ttcattctga   1260
agatatttg ccatagctgt caaggcatta tcaccggttg tgatcgcgcc tttattgtgg   1320
accgtgatat catcaatagc cgtaagatcg aactgcgtct gattaaaccg tggattaaaa   1380
gcagccatat ccgtaagaat gaagttatta agggcgaaaa attcatcatc tatagcaacc   1440
tgattgagaa tgaaaccgag tgtccgaatg cgattaaata tatcgaacag tacaagaaac   1500
gtctgatgga gcgccgcgaa tgcaaaaagg gcacgcgtaa gtggtatgaa ctgcaatggg   1560
gccgtaaacc ggaaatcttc gaagaaaaga aaattgtttt cccgtataaa agctgtgaca   1620
atcgttttgc actggataag ggtagctatt ttagcgcaga catttatagc ctggttctga   1680
agaaaaatgt gccgttcacc tatgagatcc tgctgaatat cctgaatagc ccgctgtacg   1740
agttttactt taagaccttc gcgaaaaagc tgggcgagaa tctgtacgag tactatccga   1800
acaacctgat gaagctgtgc atcccgagca tcgatttcgg cggtgagaac aatattgaga   1860
aaaagctgta tgatttcttt ggtctgacgg ataaagaaat tgagattgtg gagaagatca   1920
aagataactg ctaagaattc                                               1940
```

<210> SEQ ID NO 14
<211> LENGTH: 2781
<212> TYPE: DNA
<213> ORGANISM: Artificial Sequence
<220> FEATURE:
<223> OTHER INFORMATION: Plasmid pGS20

<400> SEQUENCE: 14

```
tttgccacct gacgtctaag aaaaggaata ttcagcaatt tgcccgtgcc gaagaaaggc     60
ccaccccgtga aggtgagcca gtgagttgat tgctacgtaa ttagttagtt agcccttagt   120
gactcgtaat acgactcact atagggctcg agtctagaga attcgatatc acccgggaac   180
tagtctgcag ccctttagtg agggttaatt ggagtcacta agggttagtt agttagatta   240
gcagaaagtc aaaagcctcc gaccggaggc ttttgactaa aacttccctt ggggttatca   300
ttggggctca ctcaaaggcg gtaatcagat aaaaaaaatc cttagctttc gctaaggatg   360
atttctgcta gagatggaat agactggatg gaggcggata agttgcagg accacttctg    420
cgctcggccc ttccggctgg ctggtttatt gctgataaat ctggagccgg tgagcgtggg   480
tctcgcggta tcattgcagc actggggcca gatggtaagc cctcccgtat cgtagttatc   540
tacacgacgg ggagtcaggc aactatggat gaacgaaata gacagatcgc tgagataggt   600
gcctcactga ttaagcattg gtaactgtca gaccaagttt actcatatat actttagatt   660
gatttaaaac ttcatttta atttaaaagg atctaggtga agatcctttt tgataatctc   720
atgaccaaaa tcccttaacg tgagttttcg ttccactgag cgtcagaccc cttaataaga   780
tgatcttctt gagatcgttt tggtctgcgc gtaatctctt gctctgaaaa cgaaaaaacc   840
```

```
gccttgcagg gcggtttttc gaaggttctc tgagctacca actctttgaa ccgaggtaac    900
tggcttggag gagcgcagtc accaaaactt gtcctttcag tttagcctta accggcgcat    960
gacttcaaga ctaactcctc taaatcaatt accagtggct gctgccagtg gtgcttttgc   1020
atgtctttcc gggttggact caagacgata gttaccggat aaggcgcagc ggtcggactg   1080
aacgggggt tcgtgcatac agtccagctt ggagcgaact gcctacccgg aactgagtgt    1140
caggcgtgga atgagacaaa cgcggccata acagcggaat gacaccggta aaccgaaagg   1200
caggaacagg agagcgcacg agggagccgc caggggaaac gcctggtatc tttatagtcc   1260
tgtcgggttt cgccaccact gatttgagcg tcagatttcg tgatgcttgt cagggggcg    1320
gagcctatgg aaaaacggct tgccgcggc cctctcactt ccctgttaag tatcttcctg    1380
gcatcttcca ggaaatctcc gccccgttcg taagccattt ccgctcgccg cagtcgaacg   1440
accgagcgta gcgagtcagt gagcgaggaa gcggaatata tcctgtatca catattctgc   1500
tgacgcaccg gtgcagcctt ttttctcctg ccacatgaag cacttcactg acaccctcat   1560
cagtgccaac atagtaagcc agtatacact ccgctagcgc tgaggtctgc ctcgtgaaga   1620
aggtgttgct gactcatacc aggcctgaat cgccccatca tccagccaga aagtgaggga   1680
gccacggttg atgagagctt tgttgtaggt ggaccagttg gtgattttga acttttgctt   1740
tgccacggaa cggtctgcgt tgtcgggaag atgcgtgatc tgatccttca actcagcaaa   1800
agttcgattt attcaacaaa gccacgttgt gtctcaaaat ctctgatgtt acattgcaca   1860
agataaaaat atatcatcat gaacaataaa actgtctgct tacataaaca gtaatacaag   1920
gggtgtttac tagaggttga tcgggcacgt aagaggttcc aactttcacc ataatgaaat   1980
aagatcacta ccgggcgtat tttttgagtt atcgagattt tcaggagcta aggaagctaa   2040
aatggagaaa aaaatcacgg gatataccac cgttgatata tcccaatggc atcgtaaaga   2100
acattttgag gcatttcagt cagttgctca atgtacctat aaccagaccg ttcagctgga   2160
tattacggcc ttttttaaaga ccgtaaagaa aaataagcac aagttttatc ggcctttat   2220
tcacattctt gcccgcctga tgaacgctca cccggagttt cgtatggcca tgaaagacgg   2280
tgagctggtg atctgggata tgttcaccc ttgttacacc gttttccatg agcaaactga   2340
aacgttttcg tccctctgga gtgaatacca cgacgatttc cggcagtttc tccacatata   2400
ttcgcaagat gtggcgtgtt acggtgaaaa cctggcctat ttccctaaag ggtttattga   2460
gaatatgttt tttgtctcag ccaatccctg ggtgagtttc accagttttg atttaaacgt   2520
ggccaatatg gacaacttct tcgcccccgt tttcacgatg gcaaatatt atacgcaagg   2580
cgacaaggtg ctgatgccgc tggcgatcca ggttcatcat gccgtttgtg atggcttcca   2640
tgtcggccgc atgcttaatg aattacaaca gtactgtgat gagtggcagg gcggggcgta   2700
ataatactag ctccggcaaa aaaacgggca aggtgtcacc accctgccct ttttctttaa   2760
aaccgaaaag attacttcgc g                                            2781
```

<210> SEQ ID NO 15
<211> LENGTH: 37
<212> TYPE: DNA
<213> ORGANISM: Artificial Sequence
<220> FEATURE:
<223> OTHER INFORMATION: Oligonucleotide fD1

<400> SEQUENCE: 15
ccgaattcgt cgacaacaga gtttgatcct ggctcag    37

```
<210> SEQ ID NO 16
<211> LENGTH: 37
<212> TYPE: DNA
<213> ORGANISM: Artificial Sequence
<220> FEATURE:
<223> OTHER INFORMATION: Oligonucleotide rP2

<400> SEQUENCE: 16
cccgggatcc aagcttacgg ctaccttgtt acgactt                                37

<210> SEQ ID NO 17
<211> LENGTH: 4709
<212> TYPE: DNA
<213> ORGANISM: Artificial Sequence
<220> FEATURE:
<223> OTHER INFORMATION: designed methylation plasmid

<400> SEQUENCE: 17
gtttgccacc tgacgtctaa gaaaaggaat attcagcaat tgcccgtgc cgaagaaagg         60 cccacccgtg aaggtgagcc agtgagttga ttgctacgta attagttagt tagcccttag       120
tgactcgtaa tacgactcac tatagggctc gaggcggccg cgcaacgcaa ttaatgtgag       180
ttagctcact cattaggcac cccaggcttt acactttatg cttccggctc gtatgttgtg       240
tggaattgtg agcggataac aatttcacac aggaaacaca tatgtttccg tgcaatgcct       300
atatcgaata tggtgataaa aatatgaaca gctttatcga agatgtggaa cagatctaca       360
acttcattaa aaagaacatt gatgtggaag aaaagatgca tttcattgaa acctataaac       420
agaaaagcaa catgaagaaa gagattagct ttagcgaaga atactataaa cagaagatta       480
tgaacggcaa aaatggcgtt gtgtacaccc cgccggaaat ggcggccttt atggttaaaa       540
atctgatcaa cgttaacgat gttattggca atccgtttat taaaatcatt gacccgagct       600
gcggtagcgg caatctgatt tgcaaatgtt ttctgtatct gaatcgcatc tttattaaga       660
acattgaggt gattaacagc aaaaataacc tgaatctgaa actggaagac atcagctacc       720
acatcgttcg caacaatctg tttggcttcg atattgacga accgcgatc aaagtgctga       780 aaattgatct gtttctgatc agcaaccaat ttagcgagaa aaatttccag gttaaagact       840
ttctggtgga aaatattgat cgcaaatatg acgtgttcat tggtaatccg ccgtatatcg       900
gtcacaaaag cgtggacagc agctacagct acgtgctgcg caaaatctac ggcagcatct       960
accgcgacaa aggcgatatc agctattgtt ctttcagaa gagcctgaaa tgtctgaagg      1020
aaggtggcaa actggtgttt gtgaccagcc gctacttctg cgagagctgc agcggtaaag      1080
aactgcgtaa attcctgatc gaaaacacga gcatttacaa gatcattgat ttttacggca      1140
tccgcccgtt caaacgcgtg gtatcgatc cgatgattat ttttctggtt cgtacgaaga      1200
actggaacaa taacattgaa attattcgcc cgaacaagat tgaaaagaac gaaaagaaca      1260
aattcctgga tagcctgttc ctggacaaaa gcgaaaagtg taaaaagttt agcattagcc      1320
agaaaagcat taataacgat ggctgggttt cgtggacga agtggagaaa acattatcg      1380 acaaaatcaa agagaaaagc aagttcattc tgaaagatat ttgccatagc tgtcaaggca      1440
ttatcaccgg ttgtgatcgc gccttttattg tggaccgtga tatcatcaat agccgtaaga      1500
tcgaactgcg tctgattaaa ccgtggatta aaagcagcca tatccgtaag aatgaagtta      1560
ttaagggcga aaaattcatc atctatagca acctgattga gaatgaaacc gagtgtccga      1620
atgcgattaa atatcgaa cagtacaaga acgtctgat ggagcgccgc gaatgcaaaa      1680
agggcacgcg taagtggtat gaactgcaat ggggccgtaa accggaaatc ttcgaagaaa      1740
```

```
agaaaattgt tttcccgtat aaaagctgtg acaatcgttt tgcactggat aagggtagct    1800
attttagcgc agacatttat agcctggttc tgaagaaaaa tgtgccgttc acctatgaga    1860
tcctgctgaa tatcctgaat agcccgctgt acgagtttta ctttaagacc ttcgcgaaaa    1920
agctgggcga gaatctgtac gagtactatc cgaacaacct gatgaagctg tgcatcccga    1980
gcatcgattt cggcggtgag aacaatattg agaaaaagct gtatgatttc tttggtctga    2040
cggataaaga aattgagatt gtggagaaga tcaaagataa ctgctaagaa ttcgatatca    2100
cccgggaact agtctgcagc cctttagtga gggttaattg gagtcactaa gggttagtta    2160
gttagattag cagaaagtca aaagcctccg accggaggct tttgactaaa acttcccttg    2220
gggttatcat tggggctcac tcaaaggcgg taatcagata aaaaaaatcc ttagctttcg    2280
ctaaggatga tttctgctag agatggaata gactggatgg aggcggataa agttgcagga    2340
ccacttctgc gctcggccct tccggctggc tggtttattg ctgataaatc tggagccggt    2400
gagcgtgggt ctcgcggtat cattgcagca ctggggccag atggtaagcc ctcccgtatc    2460
gtagttatct acacgacggg gagtcaggca actatgatga acgaaatag acagatcgct    2520 gagataggtg cctcactgat taagcattgg taactgtcag accaagttta ctcatatata    2580
ctttagattg atttaaaact tcattttaa tttaaaagga tctaggtgaa gatcctttt    2640 gataatctca tgaccaaaat cccttaacgt gagttttcgt tccactgagc gtcagacccc    2700
ttaataagat gatcttcttg agatcgtttt ggtctgcgcg taatctcttg ctctgaaaac    2760 gaaaaaccg ccttgcaggg cggttttttcg aaggttctct gagctaccaa ctctttgaac    2820
cgaggtaact ggcttggagg agcgcagtca ccaaaacttg tcctttcagt ttagccttaa    2880
ccggcgcatg acttcaagac taactcctct aaatcaatta ccagtggctg ctgccagtgg    2940
tgcttttgca tgtctttccg ggttggactc aagacgatag ttaccggata aggcgcagcg    3000
gtcggactga acgggggggtt cgtgcataca gtccagcttg gagcgaactg cctacccgga    3060
actgagtgtc aggcgtggaa tgagacaaac gcggccataa cagcggaatg acaccggtaa    3120
accgaaaggc aggaacagga gagcgcacga gggagccgcc aggggaaacg cctggtatct    3180
ttatagtcct gtcgggtttc gccaccactg atttgagcgt cagatttcgt gatgcttgtc    3240 agggggggcgg agcctatgga aaaacggctt tgccgcggcc ctctcacttc cctgttaagt    3300
atcttcctgg catcttccag gaaatctccg ccccgttcgt aagccatttc cgctcgccgc    3360
agtcgaacga ccgagcgtag cgagtcagtg agcgaggaag cggaatatat cctgtatcac    3420
atattctgct gacgcaccgg tgcagccttt tttctcctgc cacatgaagc acttcactga    3480
caccctcatc agtgccaaca tagtaagcca gtatacactc cgctagcgct gaggtctgcc    3540
tcgtgaagaa ggtgttgctg actcatacca ggcctgaatc gccccatcat ccagccagaa    3600
agtgagggag ccacggttga tgagagcttt gttgtaggtg gaccagttgg tgattttgaa    3660
cttttgcttt gccacggaac ggtctgcgtt gtcgggaaga tgcgtgatct gatccttcaa    3720
ctcagcaaaa gttcgattta ttcaacaaag ccacgttgtg tctcaaaatc tctgatgtta    3780
cattgcacaa gataaaaata tatcatcatg aacaataaaa ctgtctgctt acataaacag    3840
taatacaagg ggtgtttact agagggttgat cgggcacgta agaggttcca actttcacca    3900
taatgaaata agatcactac cgggcgtatt ttttgagtta tcgagatttt caggagctaa    3960
ggaagctaaa atggagaaaa aaatcacggg atataccacc gttgatatat cccaatggca    4020
tcgtaaagaa cattttgagg catttcagtc agttgctcaa tgtacctata accagaccgt    4080
tcagctggat attacggcct ttttaaagac cgtaaagaaa aataagcaca gtttatcc    4140
```

```
ggcctttatt cacattcttg cccgcctgat gaacgctcac ccggagtttc gtatggccat    4200
gaaagacggt gagctggtga tctgggatag tgttcaccct tgttacaccg ttttccatga    4260
gcaaactgaa acgttttcgt ccctctggag tgaataccac gacgatttcc ggcagtttct    4320
ccacatatat tcgcaagatg tggcgtgtta cggtgaaaac ctggcctatt tccctaaagg    4380
gtttattgag aatatgtttt ttgtctcagc caatccctgg gtgagtttca ccagttttga    4440
tttaaacgtg gccaatatgg acaacttctt cgcccccgtt ttcacgatgg caaatatta    4500 tacgcaaggc gacaaggtgc tgatgccgct ggcgatccag gttcatcatg ccgtttgtga    4560
tggcttccat gtcggccgca tgcttaatga attacaacag tactgtgatg agtggcaggg    4620
cggggcgtaa taatactagc tccggcaaaa aaacgggcaa ggtgtcacca ccctgccctt    4680
tttctttaaa accgaaaaga ttacttcgc                                       4709
```

<210> SEQ ID NO 18
<211> LENGTH: 458
<212> TYPE: PRT
<213> ORGANISM: Acinetobacter baylyi

<400> SEQUENCE: 18

Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

-continued

```
Leu Met Ser His Asn Ser Leu Pro Ser Lys Pro Leu Ile Ala Met Val
        275                 280                 285

Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
            340                 345                 350

Pro Ala Gly Leu Asn Ile Ile Ser Gly Met Met Pro Lys Arg Gln Ala
        355                 360                 365

Phe Asn Leu Val Ile Ser Asn Val Pro Gly Pro Arg Glu Pro Leu Tyr
    370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Glu Ile Gln Leu Phe Glu Gly Val Ile
        435                 440                 445

Ala Lys Gln Glu Asp Ile Lys Thr Ala Asn
450                 455
```

RECOMBINANT MICROORGANISMS THAT MAKE BIODIESEL

CROSS REFERENCE TO RELATED APPLICATION

This Application claims the benefit of provisional application U.S. 61/662,467 filed on Jun. 21, 2012 the contents of which are incorporated in its entirety.

TECHNICAL FIELD OF THE INVENTION

The present invention relates to recombinant microorganisms and methods for the production of biodiesel by microbial fermentation of a substrate comprising CO.

BACKGROUND OF THE INVENTION

Bacteria including carboxydotrophic acetogens *Clostridium autoethanogenum* or *C. ljungdahlii* produce fatty acids in biosynthesis of lipids and cell membranes.

In wild-type *Clostridia* strains, flux down the fatty-acid pathway is significant with lipids accounting typically for 5-6% (w/w) of the dry cell mass (respectively 1-1.5 (w/w) % of the wet cell mass) (Lepage et al., 1987, Microbiology 133: 103-110). Typically more than 95% of the lipids are in very defined C16-C18 chain length range (Lepage et al., 1987, Microbiology 133: 103-110), with 12:0, 14:0, 14:1, 16:0, 16:1, 17Δ, 18:0, 18:1, 194 fatty acids present.

Fatty acids (FAs) and their derivatives are energy dense and therefore have potential as biofuels for use as a "drop-in" transportation/jet fuel and/or for the production of other industrial chemical compounds. Examples of fatty acid derivatives include biodiesel, free fatty acids, alkenes and alkanes.

Biodiesel is a mono-alkyl ester and can be used alone in standard diesel engines, or can be blended with petrodiesel. It can also be used as a low carbon alternative to heating oil. In 2009, worldwide more than 3.5 billion gallons of biodiesel were used. Biodiesel is normally derived chemically from vegetable or animal fat by transesterification of lipids in the presence of alcohol to yield glycerine and a mono-alkyl ester. Biodiesel produced by this process can however lead to damage of diesel engines due to variations in the oils from various animal and vegtebale sources which are not very defined with a wide range of carbon chain length (Fukuda et al., 2001, *Biosci Bioeng* 92: 405-416). Critical points are dilution of motor oil, coking of piston rings, corrosion of hydraulic components, and depositions in the injection system, resulting from the production process and fuel aging, resulting in some automotive manufacturers to refuse the use of animal or vegetable derived biodiesel in some of their models (Kopke et al., 2011, The Past, Present, and Future of Biofuels—Biobutanol as Promising Alternative, In: dos Santos Bernades (Ed.) Biofuel Production-Recent Developments and Prospects, InTech, 451-486).

The current generation of biofuels that use either food or non-food crops to produce sugar or cellulose-based feedstocks may have drawbacks relating to land-use, food-security, volatility of supply and environmental issues.

It is an object of the invention to overcome these issues and provide a method of production of biodiesel, or at least to provide the public with a useful choice.

SUMMARY OF INVENTION

The invention generally provides, inter alia, methods for the production of biodiesel by microbial fermentation of a substrate comprising CO, and recombinant microorganisms of use in such methods.

In a first aspect, the invention provides a carboxydotrophic acetogenic recombinant microorganism capable of producing biodiesel and optionally one or more other products by fermentation of a substrate comprising CO.

In one particular embodiment, the microorganism is adapted to express one or more exogenous enzymes in the biodiesel biosynthesis pathway not present in a parental microorganism from which the recombinant microorganism is derived (may be referred to herein as an exogenous enzyme). In another embodiment, the microorganism is adapted to over-express one or more endogenous enzymes in the biodiesel synthesis pathway which are present in a parental microorganism from which the recombinant microorganism is derived (may be referred to herein as an endogenous enzyme).

In one embodiment, the recombinant microorganism is adapted to produce a greater amount of biodiesel than would be produced by a parental microorganism from which the recombinant microorganism is derived.

In one embodiment, the one or more enzyme that the microorganism is adapted to express or overexpress is an acyltransferase.

In one embodiment, the enzyme is an acyltransferase enzyme as defined in SEQ ID NO: 1, or a functionally equivalent variant thereof.

In one embodiment, the parental microorganism is capable of fermenting a substrate comprising CO to produce an alcohol but not of converting the alcohol to biodiesel and the recombinant microorganism is adapted to express one or more enzymes involved in the conversion of ethanol to biodiesel.

In one embodiment, the microorganism comprises one or more exogenous nucleic acids adapted to increase expression of one or more endogenous nucleic acids and which one or more endogenous nucleic acids encode one or more of the enzymes referred to herein before.

In one embodiment, the one or more exogenous nucleic acids adapted to increase expression is a regulatory element. In one embodiment, the regulatory element is a promoter. In one embodiment, the promoter is a constitutive promoter. In one embodiment, the promoter is selected from the group comprising Wood-Ljungdahl gene cluster, a pyruvate:ferredoxin oxidoreductase promoter, an Rnf complex operon promoter, ATP synthase operon promoter and Phosphotransacetylase/Acetate kinase operon promoters.

In one embodiment, the acetogenic carboxydotrophic recombinant microorganism is further adapted to express one or more exogenous enzymes in the fatty acid biosynthesis pathway. In a further aspect, the microorganism is adapted to over-express one or more endogenous enzymes in the fatty acid biosynthesis pathway.

In one embodiment, the microorganism comprises one or more exogenous nucleic acids encoding and adapted to express one or more of the enzymes referred to hereinbefore.

In one embodiment, the microorganisms comprise one or more exogenous nucleic acids encoding and adapted to express at least two of the enzymes. In other embodiments, the microorganism comprises one or more exogenous nucleic acid encoding and adapted to express five or more of the enzymes.

In one embodiment, the one or more exogenous nucleic acid is a nucleic acid construct or vector, in one particular embodiment a plasmid, encoding one or more of the enzymes referred to hereinbefore in any combination.

In one embodiment, the exogenous nucleic acid is an expression plasmid.

In one particular embodiment, the parental microorganism is selected from the group of carboxydotrophic acetogenic bacteria comprising *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* and *Thermoanaerobacter kiuvi.*

In one embodiment the parental microorganism is *Clostridium autoethanogenum* or *Clostridium ljungdahlii.* In one particular embodiment, the microorganism is *Clostridium autoethanogenum* DSM23693 a derivative of strain DSM10061. In another particular embodiment, the microorganism is *Clostridium ljungdahlii* DSM13528 (or ATCC55383).

In a second aspect, the invention provides a nucleic acid encoding one or more enzymes which when expressed in a microorganism allows the microorganism to produce biodiesel by fermentation of a substrate comprising CO.

In one embodiment, the nucleic acid encodes two or more enzymes which when expressed in a microorganism allow the microorganism to produce biodiesel by fermentation of a substrate comprising CO.

In one embodiment, the nucleic acids of the invention encode five or more such enzymes.

In one embodiment, the enzymes are chosen from the group consisting of acyl transferase and a functionally equivalent variant thereof.

In one embodiment, the nucleic acid encoding acyl transferase is SEQ ID NO: 1 or is a functionally equivalent variant thereof.

In one embodiment, the nucleic acids of the invention further comprise a promoter. In one embodiment, the promoter allows for constitutive expression of the genes under its control. In a particular embodiment a Wood-Ljungdahl cluster promoter is used. In other particular embodiments a pyruvate:ferredoxin oxidoreductase promoter, an Rnf complex operon promoter, ATP synthase operon promoter or a Phosphotransacetylase/Acetate kinase operon promoter is used. In one particular embodiment, the promoter is from *C. autoethanogenum.*

In a third aspect, the invention provides a nucleic acid construct or vector comprising one or more nucleic acid of the second aspect.

In one particular embodiment, the nucleic acid construct or vector is an expression construct or vector. In one particular embodiment, the expression construct or vector is a plasmid.

In a fourth aspect, the invention provides a host organism comprising any one or more of the nucleic acids of the second aspect or vectors or constructs of the third aspect.

In a fifth aspect, the invention provides a composition comprising an expression construct or vector as referred to in the third aspect of the invention and a methylation construct or vector.

Preferably, the composition is able to produce a recombinant microorganism according to the first aspect of the invention.

In one particular embodiment, the expression construct/vector and/or the methylation construct/vector is a plasmid.

In a sixth aspect, the invention provides a method for the production of biodiesel and optionally one or more other products by microbial fermentation comprising fermenting a substrate comprising CO using a recombinant microorganism of the first aspect of the invention.

In one embodiment the method comprises the steps of:
a. providing a substrate comprising CO to a bioreactor containing a culture of one or more microorganisms of the first aspect of the invention; and
b. anaerobically fermenting the culture in the bioreactor to produce biodiesel.

In one embodiment the method comprises the steps of:
a. capturing CO-containing gas produced as a result of an industrial process
b. anaerobic fermentation of the CO-containing gas to produce biodiesel by a culture containing one or more microorganisms of the first aspect of the invention.

In particular embodiments of the method aspects, the fermentation occurs in an aqueous culture medium.

In particular embodiments of the method aspects, the fermentation of the substrate takes place in a bioreactor.

Preferably, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

In certain embodiments the methods further comprise the step of recovering the biodiesel and optionally one or more other products from the fermentation broth.

In a seventh aspect, the invention provides biodiesel when produced by the method of the sixth aspect.

In another aspect, the invention provides a method for the production of a microorganism of the first aspect of the invention comprising transforming a carboxydotrophic acetogenic parental microorganism by introduction of one or more nucleic acids such that the microorganism is capable of producing biodiesel, or producing an increased amount of biodiesel compared to the parental microorganism, and optionally one or more other products by fermentation of a substrate comprising CO, wherein the parental microorganism is not capable of producing biodiesel, or produces biodiesel at a lower level than the recombinant microorganism, by fermentation of a substrate comprising CO.

In one particular embodiment, a parental microorganism is transformed by introducing one or more exogenous nucleic acids adapted to express one or more enzymes in the biodiesel biosynthesis pathway. In a further embodiment, a parental microorganism is further transformed by introducing one or more exogenous nucleic acids adapted to express one or more enzyme in the fatty acid biosynthesis pathway. In a further embodiment, a parental microorganism is further transformed by expressing or overexpressing one or more endogenous nucleic acids adapted to express one or more enzyme in the fatty acid biosynthesis pathway. In one embodiment, a parental microorganism is transformed with one or more nucleic acids adapted to over-express one or more endogenous enzymes in the biodiesel pathway which are naturally present in the parental microorganism.

In certain embodiments, the one or more enzymes are as herein before described.

In one embodiment a genetically engineered carboxydotrophic acetogenic bacterium comprises an exogenous nucleic acid encoding a nonspecific acetyltransferase (wax ester synthase/acyl Coenzyme A:diacylglycerol acyltransferase). The bacterium may be a *Clostridium*, including but not limited to *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum,* and *Clostridium magnum*. Other *Clostridia* species which may be used, albeit not acetogenic, include, *Clostridium acetobutylicum, Clostridium beijerinckii, C. saccharobutylicum, C. saccharoperbutylacetonicum, C. thermocellum, C. cellulolyticum, C. phytofermentans, C. kluyveri,* and *C. pasterianum*.

The bacterium may also be, for example, *Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* or *Thermoanaerobacter kiuvi*. The exogenous nonspecific acetyl transferase may be *Acinetobacter baylyi* nonspecific acetyl transferase. The nucleic acid may be on a plasmid. The nucleic acid encoding the nonspecific acetyltransferase may be codon optimized for *C. autoethanogenum* or for another host bacterium.

Another embodiment is a process for converting CO and/or $CO_2$ into biodiesel. A gaseous CO-containing and/or $CO_2$-containing substrate is passed to a bioreactor that contains a culture of carboxydotrophic, acetogenic bacteria in a culture medium. The bacteria comprise an exogenous nucleic acid encoding a nonspecific acetyltransferase (wax ester synthase/acyl Coenzyme A:diacylglycerol acyltransferase). The bacteria convert the CO and/or $CO_2$ directly to biodiesel, without the need to supply alcohols (e.g., ethanol or butanol) or fatty acids. The biodiesel is recovered from the bioreactor. The substrate may comprise an industrial waste gas. The culture may be grown and maintained strictly as anaerobically. The biodiesel may comprise fatty acid ethyl esters and/or fatty acid butyl esters.

Another embodiment is a plasmid which replicates in a carboxydotrophic acetogenic bacterium. The plasmid comprises an exogenous nucleic acid encoding a nonspecific acetyltransferase (wax ester synthase/acyl Coenzyme A:diacylglycerol acyltransferase). The nucleic acid encoding the nonspecific acetyltransferase may be codon optimized for *C. autoethanogenum*. Optionally the plasmid may be methylated, for example by passage through a bacterium that contains a desired methylase.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which.

DETAILED DESCRIPTION OF THE INVENTION

Figure 1:
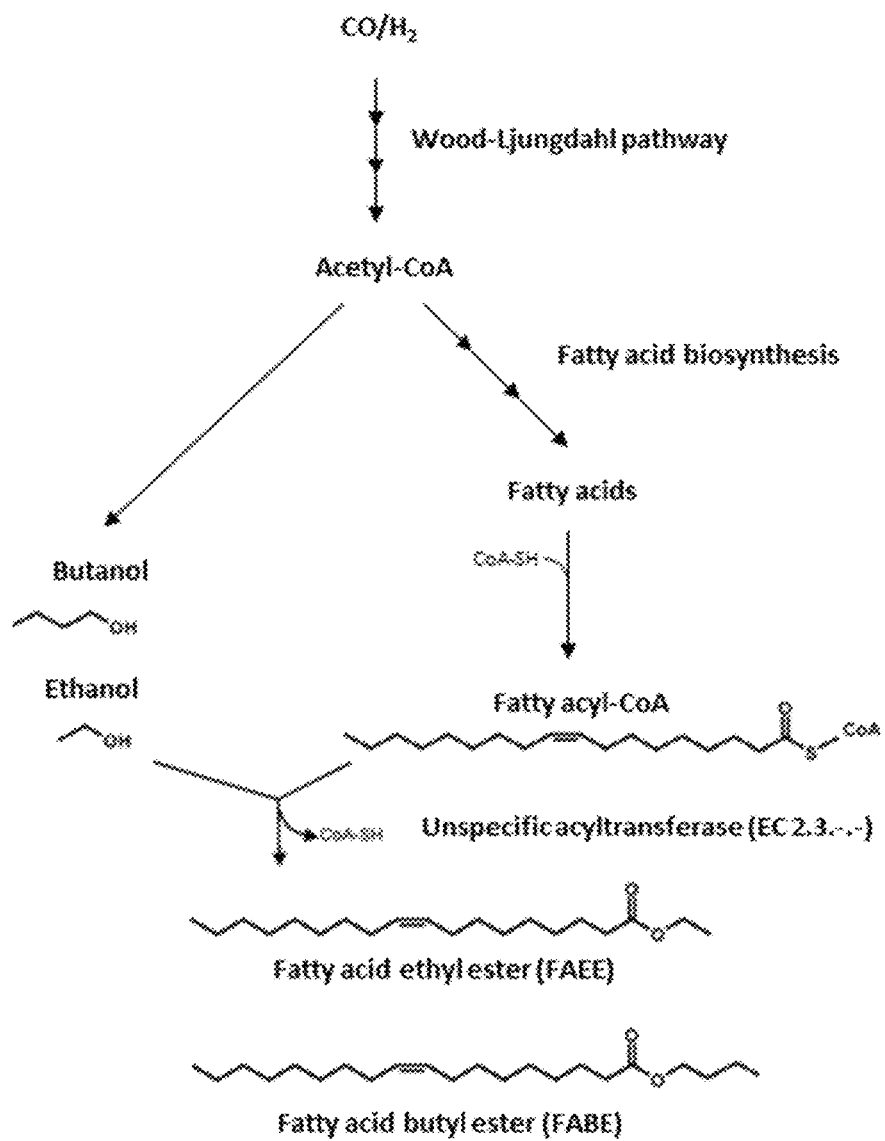
FIG. 1: Conversion of carbon monoxide and/or hydrogen to an alcohol such as ethanol or butanol, then subsequent conversion of the alcohol and a fatty acid-CoA ester to a fatty acid acylester (biodiesel) by an unspecific acyltransferase

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

As referred to herein, a "fermentation broth" is a culture medium comprising at least a nutrient media and bacterial cells.

As referred to herein, a "shuttle microorganism" is a microorganism in which a methyltransferase enzyme is expressed and is distinct from the destination microorganism.

As referred to herein, a "destination microorganism" is a microorganism in which the genes included on an expression construct/vector are expressed and is distinct from the shuttle microorganism.

The term "main fermentation product" is intended to mean the one fermentation product which is produced in the highest concentration and/or yield.

The terms "increasing the efficiency," "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO." However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting," "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

"Exogenous nucleic acids" are nucleic acids which originate outside of the microorganism to which they are introduced. Exogenous nucleic acids may be derived from any appropriate source, including, but not limited to, the microorganism to which they are to be introduced (for example in a parental microorganism from which the recombinant microorganism is derived), strains or species of microorganisms which differ from the organism to which they are to be introduced, or they may be artificially or recombinantly created. In one embodiment, the exogenous nucleic acids represent nucleic acid sequences naturally present within the microorganism to which they are to be introduced, and they are introduced to increase expression of or over-express a particular gene (for example, by increasing the copy number of the sequence (for example a gene), or introducing a strong or constitutive promoter to increase expression). In another embodiment, the exogenous nucleic acids represent nucleic acid sequences not naturally present within the microorganism to which they are to be introduced and allow for the expression of a product not naturally present within the microorganism or increased expression of a gene native to the microorganism (for example in the case of introduction of a regulatory element such as a promoter). The exogenous nucleic acid may be adapted to integrate into the genome of the microorganism to which it is to be introduced or to remain in an extra-chromosomal state.

"Exogenous" may also be used to refer to proteins. This refers to a protein that is not present in the parental microorganism from which the recombinant microorganism is derived.

The term "endogenous" as used herein in relation to a recombinant microorganism and a nucleic acid or protein refers to any nucleic acid or protein that is present in a parental microorganism from which the recombinant microorganism is derived.

"Biodiesel" as referred to herein refers to a fatty acid alkyl ester for example comprising either fatty acid ethyl ester (FAEE) and/or fatty acid butyl ester (FABE). The biodiesel produced may a mixture of fatty acid alkyl esters.

The "biodiesel biosynthesis pathway" as referred to herein refers to the pathway from fatty acyl CoA to biodiesel. Exemplary enzymes in this pathway include but are not limited to acyl transferase [EC:2.3.-.-] and acyl-CoA synthetase/long-chain-fatty-acid—CoA ligase [EC:6.2.3.1].

The "fatty acid biosynthesis pathway" refers to the pathway from acetyl CoA to the production of a fatty acyl CoA. Exemplary enzymes in this pathway include but are not limited to acetyl-CoA carboxylase/biotin carboxylase [EC:6.3.4.14/EC:6.4.1.2/EC:6.4.1.3], malonyltransferase/malonate decarboxylase [EC:2.3.1.39], fatty acid synthase [EC:2.3.1.85/EC:2.3.1.86/EC:2.3.1.-], 3-oxoacyl-[acyl-carrier-protein] synthase [EC:2.3.1.41/EC:2.3.1.179/EC:2.3.1.180], 3-oxoacyl-[acyl-carrier protein] reductase [EC:1.1.1.100], 3-hydroxymyristoyl ACP dehydrase [EC:4.2.1.-], 3-hydroxydecanoyl-[acyl-carrier-protein] dehydratase [EC:4.2.1.60], enoyl-[acyl-carrier protein] reductase [EC:1.3.1.9, EC:1.3.1.-, EC:1.3.1.-], fatty acyl-ACP thioesterase [EC:3.1.2.-3.1.2.14], oleoyl-[acyl-carrier-protein] hydrolase [EC:3.1.2.14], acyl-[acyl-carrier-protein] desaturase [EC:1.14.19.2], acetyl-CoA acyltransferase [EC:2.3.1.16], 3-hydroxyacyl-CoA dehydrogenase [EC:1.1.1.35], enoyl-CoA hydratase/long-chain 3-hydroxyacyl-CoA dehydrogenase [EC:1.1.1.211, EC:4.2.1.17], enoyl-CoA hydratase [EC:4.2.1.17], trans-2-enoyl-CoA reductase [EC:1.3.1.38], palmitoyl-protein thioesterase [EC:3.1.2.22], fatty acid elongation protein [EC:2.3.1.-], 3-ketoacyl-CoA synthase [EC:2.3.1.-], beta-keto reductase [EC:1.1.1.-], 3-hydroxy acyl-CoA dehydratase [EC:4.2.1.-], enoyl reductase [EC:1.3.1.-], palmitoyl-CoA hydrolase [EC:3.1.2.2].

It should be appreciated that the invention may be practised using nucleic acids whose sequence varies from the sequences specifically exemplified herein provided they perform substantially the same function. For nucleic acid sequences that encode a protein or peptide this means that the encoded protein or peptide has substantially the same function. For nucleic acid sequences that represent promoter sequences, the variant sequence will have the ability to promote expression of one or more genes. Such nucleic acids may be referred to herein as "functionally equivalent variants." By way of example, functionally equivalent variants of a nucleic acid include allelic variants, fragments of a gene, genes which include mutations (deletion, insertion, nucleotide substitutions and the like) and/or polymorphisms and the like. Homologous genes from other microorganisms may also be considered as examples of functionally equivalent variants of the sequences specifically exemplified herein. These include homologous genes in species such as *Clostridium acetobutylicum, Clostridium beijerinckii, C. ljungdahlii, Acinetobacter baylyi* details of which are publicly available on websites such as Genbank or NCBI. The phrase "functionally equivalent variants" should also be taken to include nucleic acids whose sequence varies as a result of codon optimisation for a particular organism. "Functionally equivalent variants" of a nucleic acid herein will preferably have at least approximately 70%, preferably approximately 80%, more preferably approximately 85%, preferably approximately 90%, preferably approximately 95% or greater nucleic acid sequence identity with the nucleic acid identified.

It should also be appreciated that the invention may be practised using polypeptides whose sequence varies from the amino acid sequences specifically exemplified herein. These variants may be referred to herein as "functionally equivalent variants." A functionally equivalent variant of a protein or a peptide includes those proteins or peptides that share at least 40%, preferably 50%, preferably 60%, preferably 70%, preferably 75%, preferably 80%, preferably 85%, preferably 90%, preferably 95% or greater amino acid identity with the protein or peptide identified and has substantially the same function as the peptide or protein of interest. Such variants include within their scope fragments of a protein or peptide wherein the fragment comprises a truncated form of the polypeptide wherein deletions may be from 1 to 5, to 10, to 15, to 20, to 25 amino acids, and may extend from residue 1 through 25 at either terminus of the polypeptide, and wherein deletions may be of any length within the region; or may be at an internal location. Functionally equivalent variants of the specific polypeptides herein should also be taken to include polypeptides expressed by homologous genes in other species of bacteria, for example as exemplified in the previous paragraph.

"Substantially the same function" as used herein is intended to mean that the nucleic acid or polypeptide is able to perform the function of the nucleic acid or polypeptide of which it is a variant. For example, a variant of an enzyme of the invention will be able to catalyse the same reaction as that enzyme. However, it should not be taken to mean that the variant has the same level of activity as the polypeptide or nucleic acid of which it is a variant.

One may assess whether a functionally equivalent variant has substantially the same function as the nucleic acid or polypeptide of which it is a variant using methods known to one of skill in the art. However, by way of example, assays to test for acyltransferase activity are described in Kalscheuer et al., 2004, Appl. Environ. Microbiol., 70: 7119-25; Stoveken et al., 2005, J. Bacteriol., 187: 1369-76.

"Over-express," "over expression" and like terms and phrases when used in relation to the invention should be taken broadly to include any increase in expression of one or more proteins (including expression of one or more nucleic acids encoding same) as compared to the expression level of the protein (including nucleic acids) of a parental microorganism under the same conditions. It should not be taken to mean that the protein (or nucleic acid) is expressed at any particular level.

A "parental microorganism" is a microorganism used to generate a recombinant microorganism of the invention. The parental microorganism may be one that occurs in nature (ie a wild type microorganism) or one that has been previously modified but which does not express or over-express one or more of the enzymes the subject of the present invention. Accordingly, the recombinant microorganisms of the invention may have been modified to express or over-express one or more enzymes that were not expressed or over-expressed in the parental microorganism.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

The inventors have surprisingly shown that a recombinant microorganism can be engineered to produce a biodiesel from a CO-containing substrate. The inventors have engineered recombinant organisms and invented methods of use thereof for the production of the fatty acid derivative biodiesel. The inventors also contemplate that other fatty acid derivatives including free fatty acids, alkanes and alkenes could be produced as part of the invention. All these products can be derived from fatty acid key intermediates fatty acid acyl-CoA (thioesters with CoA) or fatty acid ACPs (Acyl carrier proteins).

The biodiesel produced by the invention is a long-chain, energy dense compound, and its synthesis requires the cell to invest energy in the form of nucleoside triposphates such as ATP. In an aerobic process and/or using sugar as a substrate requires sufficient energy to be supplied from glycolysis to yield several molecules of ATP. The production of biodiesel via the fatty acid biosynthesis pathway in an aerobic process and/or using sugar as a substrate proceeds in a relatively straightforward manner due to the C5 pentose and C6 hexose molecules which are converted into longer chain fatty acids driven by the high ATP availability although a large number of reactions are required. The present invention may have advantages over producing biofuels from sugar based substrates and provides an alternative means for the production of biodiesel utilising waste gases including carbon monoxide from industrial processes.

For anaerobic acetogens using a C1 substrate like CO or CO2, it is more difficult to build up long molecules such as fatty acids as unlike in glycolysis, no net energy is gained from substrate-level phosphorylation in the carbon fixating Wood-Ljungdahl pathway, in fact activation of CO2 to formate even requires one molecule of ATP and a membrane gradient is required. To date the product with most carbon atoms reported in acetogens (both native and recombinant organisms) are C4 compounds butanol and 2,3-butanediol.

The inventors have shown that it is possible to produce these longer chain fatty acid molecules such as biodiesel using the C1 feedstock CO via the acetyl CoA intermediate. As the substrate CO or CO2 is in the Wood-Ljungdahl pathway directly channelled into acetyl-CoA (the starting point of the fatty acid biosynthesis), fewer reactions and enzymes are needed as from sugar via glycolysis, making the process faster and more efficient even though less ATP is available. Though less ATP is available in carboxydotrophic acetogens, the inventors consider that this more direct pathway may sustain a higher metabolic flux (owing to higher chemical motive force of intermediate reactions).

In a particular embodiment of the invention, the inventors have found that the production of biodiesel (a fatty acid alkyl ester) by a recombinant microorganism of the invention is enabled by introduction to the microorganism of an exogenous acyl transferase. Traditional methods of production of biodiesel involve the transesterification of a lipid (triglyceride) in the presence of alcohol to yield glycerine and biodiesel. However, the present invention provides a recombinant microorganism that is able to co-produce both alcohol (including ethanol and/or butanol) as well as fatty acid. The inventors believe that this co-production provides the requisite substrates to provide a driving force for the in vivo production of biodiesel comprising either FAEE (Fatty acid ethyl esters) and/or FABE (Fatty acid butyl esters).

To achieve an embodiment of the invention, an unspecific acyltransferase (wax ester synthase/acyl Coenzyme A: diacylglycerol acyltransferase) from *Acinetobacter baylyi* was introduced to the acetogenic microorganism. The microorganism produces an alcohol (for example ethanol or butanol) and a fatty acyl-CoA which are converted to a fatty acid alkyl ester (i.e. biodiesel) (FIG. 1) (Kalscheuer et al., 2004, *Appl. Environ. Microbiol.*, 70: 7119-25; Stoveken et al., 2005, *J. Bacteriol.*, 187: 1369-76). Fatty acid acyl-CoAs are a direct product of fatty acids and are produced by the action of for example acyl-CoA synthetase (long-chain-fatty-acid—CoA ligase) which may be present in carboxydotrophic acetogens. In vivo production of FAEE using this enzyme has not been shown except with supplemental fatty acids or alcohol being supplied to the reaction externally (Kalscheuer et al., 2006, *Microbiology*, 152, 2529-36). While all organisms produce fatty acid precursors, for organisms that don't produce (high amounts of) alcohols like *E. coli*, additional genetic modifications become necessary. Bacterial production of FABE has not been demonstrated previously at all. The present invention does not require such external supply of alcohol therefore may provide a number of advantages. Included in these advantages is the reduction in the cost of feedstock, a significant reduction in complexity of the equipment and parameter control and limited handling and separation steps required by the process.

While the inventors have demonstrated the efficacy of the invention in *Clostridium* autoethanogenum, they contemplate that the invention is applicable to the wider group of carboxydotrophic acteogenic microorganisms and discussed further herein.

Microorganisms

As discussed hereinbefore, the invention provides a recombinant microorganism capable of producing biodiesel, and optionally one or more other products, by fermentation of a substrate comprising CO.

In one particular embodiment, the microorganism is adapted to express one or more exogenous enzymes in the biodiesel biosynthesis pathway. In another embodiment, the microorganism is adapted to over-express one or more endogenous enzymes in the biodiesel biosynthesis pathway.

In one embodiment, the recombinant microorganism is adapted to produce a greater amount of biodiesel than would be produced by a parental microorganism from which the recombinant microorganism is derived.

In one embodiment, the parental microorganism from which the recombinant microorganism is derived is capable of fermenting a substrate comprising CO to produce an alcohol but not of converting the alcohol to a biodiesel, and the recombinant microorganism is adapted to express one or more enzymes involved in the conversion of ethanol to biodiesel.

In one embodiment, the acetogenic carboxydotrophic recombinant microorganism is further adapted to express one or more exogenous enzymes in the fatty acid biosynthesis pathway. In a further aspect, the microorganism is further adapted to over-express one or more endogenous enzymes in the fatty acid biosynthesis pathway.

The microorganism may be adapted to express or over-express the one or more enzymes by any number of recombinant methods including, for example, increasing expression of endogenous genes (for example, by introducing a stronger or constitutive promoter to drive expression of a gene), increasing the copy number of a gene encoding a particular enzyme by introducing exogenous nucleic acids encoding and adapted to express the enzyme, or introducing an exogenous nucleic acid encoding and adapted to express an enzyme not naturally present within the parental microorganism.

In certain embodiments, the parental microorganism may be transformed to provide a combination of a) increased or over-expression of one or more endogenous genes and b) introduction of one or more exogenous genes. For example, one or more genes encoding one or more enzymes in the biodiesel and optionally the fatty acid biosynthesis pathway may be native to the parental microorganism but it may not include one or more other genes encoding one or more other enzymes in the pathway.

In one embodiment the one or more enzymes in the biodiesel biosynthesis pathway are chosen from the group consisting of acyl transferase and a functionally equivalent variant thereof. By way of example only, sequence information for acyl transferase is provided.

The enzymes and functional variants of use in the microorganisms of the invention may be derived from any appropriate source, including different genera and species of bacteria, or other organisms. However, in one embodiment, the acyl transferase is that derived from *Acinetobacter baylyi* as described in SEQ ID NO: 1, or a functionally equivalent variant thereof. In a particular embodiment, the acyl transferase has the identifying characterisitics of the unspecific acyltransferase YP_045555.1; Gene ID: 2879218 of *Acinetobacter baylyi*. An acyl-CoA synthetase/long-chain-fatty-acid—CoA ligase is for example given under accession numbers P69451 or GeneID: 946327.

In one embodiment, the microorganism comprises one or more exogenous nucleic acids adapted to increase expression of one or more nucleic acids native to the parental microorganism and which one or more nucleic acids encode one or more of the enzymes referred to herein before. In one embodiment, the one or more exogenous nucleic acid adapted to increase expression is a regulatory element. In one embodiment, the regulatory element is a promoter. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster, a pyruvate:ferredoxin oxidoreductase promoter, an Rnf complex operon promoter, ATP synthase operon promoter or Phosphotransacetylase/Acetate kinase operon promoters. It will be appreciated by those of skill in the art that other promoters which can direct expression, preferably a high level of expression under appropriate fermentation conditions, would be effective as alternatives to the exemplified embodiments.

In one embodiment, the microorganism comprises one or more exogenous nucleic acids encoding and adapted to express one or more of the enzymes referred to herein before. In one embodiment, the microorganisms comprise one or more exogenous nucleic acids encoding and adapted to express at least two of the enzymes. In other embodiments, the microorganism comprises one or more exogenous nucleic acid encoding and adapted to express three of the enzymes. In other embodiments, the microorganism comprises one or more exogenous nucleic acid encoding and adapted to express five of the enzymes.

In one particular embodiment, the microorganism comprises one or more exogenous nucleic acids encoding an acyl transferase or a functionally equivalent variant thereof.

In one embodiment, the acyl transferase is encoded by the nucleic acid sequence exemplified in SEQ ID NO: 1, or a functionally equivalent variant thereof.

The microorganism may comprise one or more exogenous nucleic acids. Where it is desirable to transform the parental microorganism with two or more genetic elements (such as genes or regulatory elements (for example a promoter)) they may be contained on one or more exogenous nucleic acids.

In one embodiment, the one or more exogenous nucleic acid is a nucleic acid construct or vector, in one particular embodiment a plasmid, encoding one or more of the enzymes referred to hereinbefore in any combination.

The exogenous nucleic acids may remain extra-chromosomal upon transformation of the parental microorganism or may intergrate into the genome of the parental microorganism. Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences).

In one embodiment, the exogenous nucleic acids encoding one or enzymes as mentioned herein before will further comprise a promoter adapted to promote expression of the one or more enzymes encoded by the exogenous nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster, a pyruvate:ferredoxin oxidoreductase promoter, an Rnf complex operon promoter, ATP synthase operon promoter and Phosphotransacetylase/Acetate kinase promoters. It will be appreciated by those of skill in the art that other promoters which can direct expression, preferably a high level of expression under appropriate fermentation conditions, would be effective as alternatives to the exemplified embodiments.

In one embodiment, the exogenous nucleic acid is an expression plasmid.

In one embodiment, the parental carboxydotrophic acetogenic microorganism is selected from the group consisting of *Clostridium autoethanogenum*, *Clostridium ljungdahlii*, *Clostridium ragsdalei*, *Clostridium carboxidivorans*, *Clostridium drakei*, *Clostridium scatologenes*, *Butyribacterium limosum*, *Butyribacterium methylotrophicum*, *Acetobacterium woodii*, *Alkalibaculum bacchii*, *Blautia producta*, *Eubacterium limosum*, *Moorella thermoacetica*, *Moorella thermautotrophica*, *Oxobacter pfennigii*, and *Thermoanaerobacter kiuvi*.

In one particular embodiment of the first or second aspects, the parental microorganism is selected from the group of carboxydotrophic *Clostridia* comprising *Clostridium autoet-* *hanogenum*, *Clostridium ljungdahlii*, *Clostridium ragsdalei*, *Clostridium carboxidivorans*, *Clostridium drakei*, *Clostridium scatologenes*, *Clostridium aceticum*, *Clostridium formicoaceticum*, *Clostridium magnum*.

In a one embodiment, the microorganism is selected from a cluster of carboxydotrophic *Clostridia* comprising the species *C. autoethanogenum*, *C. ljungdahlii*, and "*C. ragsdalei*" and related isolates. These include but are not limited to strains *C. autoethanogenum* JAI-1$^T$ (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), or "*C. ragsdalei* P11$^T$" (ATCC BAA-622) (WO 2008/028055), and related isolates such as "*C. coskatii*" (US patent 2011/0229947), "*Clostridium* sp. MT351" (Michael Tyurin & Kiriukhin, 2012) and mutant strains thereof such as *C. ljungdahlii* OTA-1 (Tirado-Acevedo O. Production of Bioethanol from Synthesis Gas Using *Clostridium ljungdahlii*. PhD thesis, North Carolina State University, 2010).

These strains form a subcluster within the Clostridial rRNA cluster I (Collins et al., 1994), having at least 99% identity on 16S rRNA gene level, although being distinct species as determined by DNA-DNA reassociation and DNA fingerprinting experiments (WO 2008/028055, US patent 2011/0229947).

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Kopke et al., 2010) and a GC composition of around 32% mol (Abrini et al., 1994; Kopke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde:ferredoxin oxidoreductase (Kopke et al., 2010, 2011). The organization and number of Wood-Ljungdahl pathway genes, responsible for gas uptake, has been found to be the same in all species, despite differences in nucleic and amino acid sequences (Köpke et al., 2011).

The strains all have a similar morphology and size (logarithmic growing cells are between 0.5-0.7×3-5 µm), are mesophilic (optimal growth temperature between 30-37° C.) and strictly anaerobe (Abrini et al., 1994; Tanner et al., 1993) (WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et al., 1994; Kopke et al., 2011; Tanner et al., 1993) However, the species differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotroph to certain vitamins (e.g. thiamine, biotin) while others were not. Reduction of carboxylic acids into their corresponding alcohols has been shown in a range of these organisms (Perez, Richter, Loftus, & Angenent, 2012).

The traits described are therefore not specific to one organism like *C. autoethanogenum* or *C. ljungdahlii*, but rather general traits for carboxydotrophic, ethanol-synthesizing *Clostridia*. Thus, the invention can be anticipated to work across these strains, although there may be differences in performance.

The recombinant carboxydotrophic acetogenic microorganisms of the invention may be prepared from a parental carboxydotrophic acetogenic microorganism and one or more exogenous nucleic acids using any number of techniques known in the art for producing recombinant microorganisms. By way of example only, transformation (including transduction or transfection) may be achieved by electroporation, electrofusion, ultrasonication, polyethylene glycol-mediated transformation, conjugation, or chemical and natural competence. Suitable transformation techniques are described for example in Sambrook J, Fritsch E F, Maniatis T: Molecular Cloning: A laboratory Manual, Cold Spring Harbour Labrotary Press, Cold Spring Harbour, 1989.

Electroporation has been described for several carboxydotrophic acetogens as *C. ljungdahlii* (Köpke et al., 2010; Leang, Ueki, Nevin, & Lovley, 2012) (PCT/NZ2011/000203; WO2012/053905), *C. autoethanogenum* (PCT/NZ2011/000203; WO2012/053905), *Acetobacterium woodii* (Stratz, Sauer, Kuhn, & Dune, 1994) or *Moorella thermoacetica* (Kita et al., 2012) and is a standard method used in many *Clostridia* such as *C. acetobutylicum* (Mermelstein, Welker, Bennett, & Papoutsakis, 1992), *C. cellulolyticum* (Jennert, Tardif, Young, & Young, 2000) or *C. thermocellum* (M V Tyurin, Desai, & Lynd, 2004).

Electrofusion has been described for acetogenic *Clostridium* sp. MT351 (Tyurin and Kiriukhin, 2012).

Prophage induction has been described for carboxydotrophic acetogen as well in case of *C. scatologenes* (Prasanna Tamarapu Parthasarathy, 2010, Development of a Genetic Modification System in *Clostridium scatologenes* ATCC 25775 for Generation of Mutants, Masters Project Western Kentucky University).

Conjugation has been described as method of choice for acetogen *Clostridium difficile* (Herbert, O'Keeffe, Purdy, Elmore, & Minton, 2003) and many other *Clostridia* including *C. acetobuylicum* (Williams, Young, & Young, 1990).

In one embodiment, the parental strain uses CO as its sole carbon and energy source.

In one embodiment the parental microorganism is *Clostridium autoethanogenum* or *Clostridium ljungdahlii*. In one particular embodiment, the microorganism is *Clostridium autoethanogenum* DSM23693. In another particular embodiment, the microorganism is *Clostridium ljungdahlii* DSM13528 (or ATCC55383).

Nucleic Acids

The invention also provides one or more nucleic acids or nucleic acid constructs of use in generating a recombinant microorganism of the invention.

In one embodiment, the nucleic acids comprises sequences encoding one or more of the enzymes in the biodiesel biosynthesis pathway which when expressed in a microorganism allows the microorganism to produce biodiesel by fermentation of a substrate comprising CO. In one particular embodiment, the invention provides a nucleic acid encoding two or more enzymes which when expressed in a microorganism allows the microorganism to produce biodiesel by fermentation of a substrate comprising CO. In one embodiment, the nucleic acids of the invention encode three such enzymes, or five such enzymes.

In one particular embodiment, the enzymes are chosen from the group consisting of acyl transferase and a functionally equivalent variant thereof.

Exemplary amino acid sequences and nucleic acid sequences encoding enzymes described herein are provided herein or can be obtained from GenBank as mentioned hereinbefore. However, skilled persons will readily appreciate alternative nucleic acids sequences encoding the enzymes or functionally equivalent variants thereof, having regard to the information contained herein, in GenBank and other databases, and the genetic code.

In one embodiment, the acyl transferase is encoded by the sequence of SEQ ID NO: 1 or a functionally equivalent variant thereof.

In one embodiment, the nucleic acid further encodes one or more exogenous enzymes in the fatty acid biosynthesis pathway. In a further aspect, the nucleic acid further encodes one or more endogenous enzymes in the fatty acid biosynthesis pathway.

In one embodiment, the nucleic acids of the invention will further comprise a promoter. In one embodiment, the promoter allows for constitutive expression of the genes under its control. However, inducible promoters may also be employed. Persons of skill in the art will readily appreciate promoters of use in the invention. Preferably, the promoter can direct a high level of expression under appropriate fermentation conditions. In a particular embodiment a Wood-Ljungdahl cluster promoter is used. In another embodiment, a Phosphotransacetylase/Acetate kindase promoter is used. In another embodiment a pyruvate:ferredoxin oxidoreductase promoter, an Rnf complex operon promoter or an ATP synthase operon promoter. In one particular embodiment, the promoter is from *C. autoethanogenum*.

The nucleic acids of the invention may remain extra-chromosomal upon transformation of a parental microorganism or may be adapted for integration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acid is nucleic acid construct or vector. In one particular embodiment, the nucleic acid construct or vector is an expression construct or vector, however other constructs and vectors, such as those used for cloning are encompassed by the invention. In one particular embodiment, the expression construct or vector is a plasmid.

It will be appreciated that an expression construct/vector of the present invention may contain any number of regulatory elements in addition to the promoter as well as additional genes suitable for expression of further proteins if desired. In one embodiment the expression construct/vector includes one promoter. In another embodiment, the expression construct/vector includes two or more promoters. In one particular embodiment, the expression construct/vector includes one promoter for each gene to be expressed. In one embodiment, the expression construct/vector includes one or more ribosomal binding sites, preferably a ribosomal binding site for each gene to be expressed.

It will be appreciated by those of skill in the art that the nucleic acid sequences and construct/vector sequences described herein may contain standard linker nucleotides such as those required for ribosome binding sites and/or restriction sites. Such linker sequences should not be interpreted as being required and do not provide a limitation on the sequences defined.

Nucleic acids and nucleic acid constructs, including expression constructs/vectors of the invention may be constructed using any number of techniques standard in the art. For example, chemical synthesis or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pMTL80000 vectors, pIMP1, pJIR750, and the plasmids exemplified in the Examples section herein after.

It should be appreciated that nucleic acids of the invention may be in any appropriate form, including RNA, DNA, or cDNA.

The invention also provides host organisms, particularly microorganisms, and including viruses, bacteria, and yeast, comprising any one or more of the nucleic acids described herein.

Method of Producing Microorganisms

The one or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, ultrasonication, polyethylene glycol-mediated transformation, chemical or natural competence, protoplast transformation, prophage induction or conjugation. Suitable transformation techniques are described for example in, Sambrook J, Fritsch E F, Maniatis T: Molecular Cloning: A laboratory Manual, Cold Spring Harbour Labrotary Press, Cold Spring Harbour, 1989.

Electroporation has been described for several carboxydotrophic acetogens as *C. ljungdahlii* (Köpke et al. 2010, *Poc. Nat. Acad. Sci. U.S.A.* 107: 13087-92; PCT/NZ2011/000203; WO2012/053905), *C. autoethanogenum* (PCT/NZ2011/000203; WO2012/053905), or *Acetobacterium woodii* (Straetz et al., 1994, *Appl. Environ. Microbiol.* 60:1033-37) and is a standard method used in many *Clostridia* such as *C. acetobutylicum* (Mermelstein et al., 1992, *Biotechnology*, 10, 190-195), *C. cellulolyticum* (Jennert et al., 2000, *Microbiology*, 146: 3071-3080) or *C. thermocellum* (Tyurin et al., 2004, *Appl. Environ. Microbiol.* 70: 883-890). Prophage induction has been demonstrated for carboxydotrophic acetogen as well in case of *C. scatologenes* (Prasanna Tamarapu Parthasarathy, 2010, Development of a Genetic Modification System in *Clostridium scatologenes* ATCC 25775 for Generation of Mutants, Masters Project Western Kentucky University), while conjugation has been described as method of choice for many *Clostridia* including *Clostridium difficile* (Herbert et al., 2003, *FEMS Microbiol. Lett.* 229: 103-110) or *C. acetobuylicum* (Williams et al., 1990, *J. Gen. Microbiol.* 136: 819-826) and could be used in a similar fashion for carboxydotrophic acetogens.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:

introduction into a shuttle microorganism of (i) of an expression construct/vector as described herein and (ii) a methylation construct/vector comprising a methyltransferase gene;

expression of the methyltransferase gene;

isolation of one or more constructs/vectors from the shuttle microorganism; and, introduction of the one or more construct/vector into a destination microorganism.

In one embodiment, the methyltransferase gene is expressed constitutively. In another embodiment, expression of the methyltransferase gene of is induced.

The shuttle microorganism is a microorganism, preferably a restriction negative microorganism, that facilitates the methylation of the nucleic acid sequences that make up the expression construct/vector. In a particular embodiment, the shuttle microorganism is a restriction negative *E. coli*, *Bacillus subtillis*, or *Lactococcus lactis*.

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter and is induced by addition of lactose or an analogue thereof, more preferably isopropyl-β-D-thiogalactoside (IPTG). Other suitable promoters include the ara, tet, or T7 system. In a further embodiment of the invention, the methylation construct/vector promoter is a constitutive promoter.

In a particular embodiment, the methylation construct/vector has an origin of replication specific to the identity of the shuttle microorganism so that any genes present on the methylation construct/vector are expressed in the shuttle microorganism. Preferably, the expression construct/vector has an origin of replication specific to the identity of the destination microorganism so that any genes present on the expression construct/vector are expressed in the destination microorganism.

Expression of the methyltransferase enzyme results in methylation of the genes present on the expression construct/vector. The expression construct/vector may then be isolated from the shuttle microorganism according to any one of a number of known methods. By way of example only, the methodology described in the Examples section described hereinafter may be used to isolate the expression construct/vector.

In one particular embodiment, both construct/vector are concurrently isolated.

The expression construct/vector may be introduced into the destination microorganism using any number of known methods. However, by way of example, the methodology described in the Examples section hereinafter may be used. Since the expression construct/vector is methylated, the nucleic acid sequences present on the expression construct/vector are able to be incorporated into the destination microorganism and successfully expressed.

It is envisaged that a methyltransferase gene may be introduced into a shuttle microorganism and over-expressed. Thus, in one embodiment, the resulting methyltransferase enzyme may be collected using known methods and used in vitro to methylate an expression plasmid. The expression construct/vector may then be introduced into the destination microorganism for expression. In another embodiment, the methyltransferase gene is introduced into the genome of the shuttle microorganism followed by introduction of the expression construct/vector into the shuttle microorganism, isolation of one or more constructs/vectors from the shuttle microorganism and then introduction of the expression construct/vector into the destination microorganism.

It is envisaged that the expression construct/vector and the methylation construct/vector as defined above may be combined to provide a composition of matter. Such a composition has particular utility in circumventing restriction barrier mechanisms to produce the recombinant microorganisms of the invention.

In one particular embodiment, the expression construct/vector and/or the methylation construct/vector are plasmids.

Persons of ordinary skill in the art will appreciate a number of suitable methyltransferases of use in producing the microorganisms of the invention. However, by way of example the *Bacillus subtilis* phage ΦT1 methyltransferase and the methyltransferase described in the Examples herein after may be used. In one embodiment, the methyltransferase has the amino acid sequence of SEQ ID NO: 12, or is a functionally equivalent variant thereof. Nucleic acids encoding suitable methyltransferases will be readily appreciated having regard to the sequence of the desired methyltransferase and the genetic code. In one embodiment, the nucleic acid encoding a methyltransferase is as described in the Examples herein after (for example the nucleic acid of SEQ ID NO: 17, or it is a functionally equivalent variant thereof).

Any number of constructs/vectors adapted to allow expression of a methyltransferase gene may be used to generate the methylation construct/vector. However, by way of example, the plasmid described in the Examples section hereinafter may be used (for example, SEQ ID NO: 14).

Methods of Production

The invention provides a method for the production of biodiesel, and optionally one or more other products, by microbial fermentation comprising fermenting a substrate comprising CO using a recombinant microorganism of the invention. The methods of the invention may be used to reduce the total atmospheric carbon emissions from an industrial process.

Preferably, the fermentation comprises the steps of anaerobically fermenting a substrate in a bioreactor to produce at least biodiesel using a recombinant microorganism of the invention.

In one embodiment the method comprises the steps of:
a. providing a substrate comprising CO to a bioreactor containing a culture of one or more microorganisms of the invention; and
b. anaerobically fermenting the culture in the bioreactor to produce at least biodiesel.

In one embodiment the method comprises the steps of:
a. capturing CO-containing gas produced as a result of an industrial process;
b. anaerobic fermentation of the CO-containing gas to produce biodiesel by a culture containing one or more microorganisms of the invention.

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing biodiesel for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and the production of biodiesel to occur, in addition to the CO-containing substrate gas, a suitable liquid nutrient medium will need to be fed to the bioreactor.

In particular embodiments of the method aspects, the fermentation occurs in an aqueous culture medium. In particular embodiments of the method aspects, the fermentation of the substrate takes place in a bioreactor.

The substrate and media may be fed to the bioreactor in a continuous, batch or batch fed fashion. A nutrient medium will contain vitamins and minerals sufficient to permit growth of the micro-organism used. Anaerobic media suitable for fermentation using CO are known in the art. For example, suitable media are described Biebel (2001). In one embodiment of the invention the media is as described in the Examples section herein after.

The fermentation should desirably be carried out under appropriate fermentation conditions for the production of biodiesel to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of fermentation. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure.

Also, since a given CO-to-biodiesel conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that one or more product is consumed by the culture.

The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

Biodiesel, or a mixed stream containing biodiesel and/or one or more other products, may be recovered from the fermentation broth by methods known in the art, such as fractional distillation or evaporation, pervaporation, gas stripping and extractive fermentation, including for example, liquid-liquid extraction. Products may also diffuse or secrete into media, from which they can extracted by phase separation.

In certain preferred embodiments of the invention, biodiesel and one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

The invention will now be described in more detail with reference to the following non-limiting examples.

Example 1

Production of Biodiesel from CO

An acetogenic carboxydotroph *Clostridium autoethanogenum* was engineered with the unspecific acyltransferase of *Acinetobacter baylyi* for production of a biodiesel fatty acid acyl ester, butanoic acid butyl ester (FABE). Production of butanol was demonstrated earlier using a genetically modified strain of *Clostridium autoethanogenum* (WO 2012/053905).

Strains and Growth Conditions:

All subcloning steps were performed in *E. coli* using standard strains and growth conditions as described earlier (Sambrook et al, Molecular Cloning: A laboratory Manual, Cold Spring Harbour Labrotary Press, Cold Spring Harbour, 1989; Ausubel et al, Current protocols in molecular biology, John Wiley & Sons, Ltd., Hoboken, 1987).

*C. autoethanogenum* DSM10061 and DSM23693 (a derivative of DSM10061) were obtained from DSMZ (The German Collection of Microorganisms and Cell Cultures, Inhoffenstraβe 7 B, 38124 Braunschweig, Germany). Growth was carried out at 37° C. using strictly anaerobic conditions and techniques (Hungate, 1969, Methods in Microbiology, vol. 3B. Academic Press, New York: 117-132; Wolfe, 1971, Adv. Microb. Physiol., 6: 107-146). Chemically defined PETC media without yeast extract (Tab. 1) and 30 psi carbon monioxide containing steel mill waste gas (collected from New Zealand Steel site in Glenbrook, NZ; composition: 44% CO, 32% N2, 22% CO2, 2% H2) as sole carbon and energy source was used.

TABLE 1

| PETC medium | |
|---|---|
| Media component | Concentration per 1.0 L of media |
| NH4Cl | 1 g |
| KCl | 0.1 g |
| MgSO4•7H2O | 0.2 g |
| NaCl | 0.8 g |
| KH2PO4 | 0.1 g |
| CaCl2 | 0.02 g |
| Trace metal solution | 10 ml |
| Wolfe's vitamin solution | 10 ml |
| Resazurin (2 g/L stock) | 0.5 ml |
| NaHCO3 | 2 g |
| Reducing agent | 0.006-0.008% (v/v) |
| Distilled water | Up to 1 L, pH 5.5 (adjusted with HCl) |
| Wolfe's vitamin solution | per L of Stock |
| Biotin | 2 mg |
| Folic acid | 2 mg |

TABLE 1-continued

| PETC medium | |
|---|---|
| Pyridoxine hydrochloride | 10 mg |
| Riboflavin | 5 mg |
| Nicotinic acid | 5 mg |
| Calcium D-(+)-pantothenate | 5 mg |
| Vitamin B12 | 0.1 mg |
| p-Aminobenzoic acid | 5 mg |
| Lipoic acid | 5 mg |
| Thiamine | 5 mg |
| Distilled water | To 1 L |
| Trace metal solution | per L of stock |
| Nitrilotriacetic Acid | 2 g |
| MnSO4•H2O | 1 g |
| Fe (SO4)2(NH4)2•6H2O | 0.8 g |
| CoCl2•6H2O | 0.2 g |
| ZnSO4•7H2O | 0.2 mg |
| CuCl2•2H2O | 0.02 g |
| NaMoO4•2H2O | 0.02 g |
| Na2SeO3 | 0.02 g |
| NiCl2•6H2O | 0.02 g |
| Na2WO4•2H2O | 0.02 g |
| Distilled water | To 1 L |
| Reducing agent stock | per 100 mL of stock |
| NaOH | 0.9 g |
| Cystein•HCl | 4 g |
| Na2S | 4 g |
| Distilled water | To 100 mL |

Construction of Expression Plasmid:

Standard Recombinant DNA and molecular cloning techniques were used in this invention and are described by Sambrook et al, 1989 and Ausubel et al, 1987. The unspecific acyltransferase (YP_045555.1; Gene ID: 2879218) of *Acinetobacter baylyi* was codon optimized and synthesized (SEQ ID NO: 1).

Genomic DNA from *Clostridum autoethanogenum* DSM 10061 was isolated using a modified method by Bertram and Dürre (1989). A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 300 µl lysozyme (~100,000 U) were added and the mixture was incubated at 37° C. for 30 min, followed by addition of 280 µl of a 10% (w/v) SDS solution and another incubation for 10 min. RNA was digested at room temperature by addition of 240 µl of an EDTA solution (0.5 M, pH 8), 20 µl Tris-HCl (1 M, pH 7.5), and 10 µl RNase A (Fermentas). Then, 100 µl Proteinase K (0.5 U) were added and proteolysis took place for 1-3 h at 37° C. Finally, 600 µl of sodium perchlorate (5 M) were added, followed by a phenol-chloroform extraction and an isopropanol precipitation. DNA quantity and quality was inspected spectrophotometrically.

The phosphotransacetylase/acetate kinase promoter region of *C. autoethanogenum* (SEQ ID NO: 4) was amplified by PCR from genomic DNA with oligonucleotides Ppta-ack-NotI-F (SEQ ID NO: 2: GAGCGGCCGCAATATGATATT-TATGTCC) and Ppta-ack-NdeI-R (SEQ ID NO: 3: TTC-CATATGTTTCATGTTCATTTCCTCC) and iProof High Fidelity DNA Polymerase (Bio-Rad Labratories) applying the following program: initial denaturation at 98° C. for 30 seconds, followed by 35 cycles of denaturation (98° C. for 10 seconds), annealing (55° C. for 30 seconds) and elongation (72° C. for 30 seconds), before a final extension step (72° C. for 10 minutes).

Figure 2:
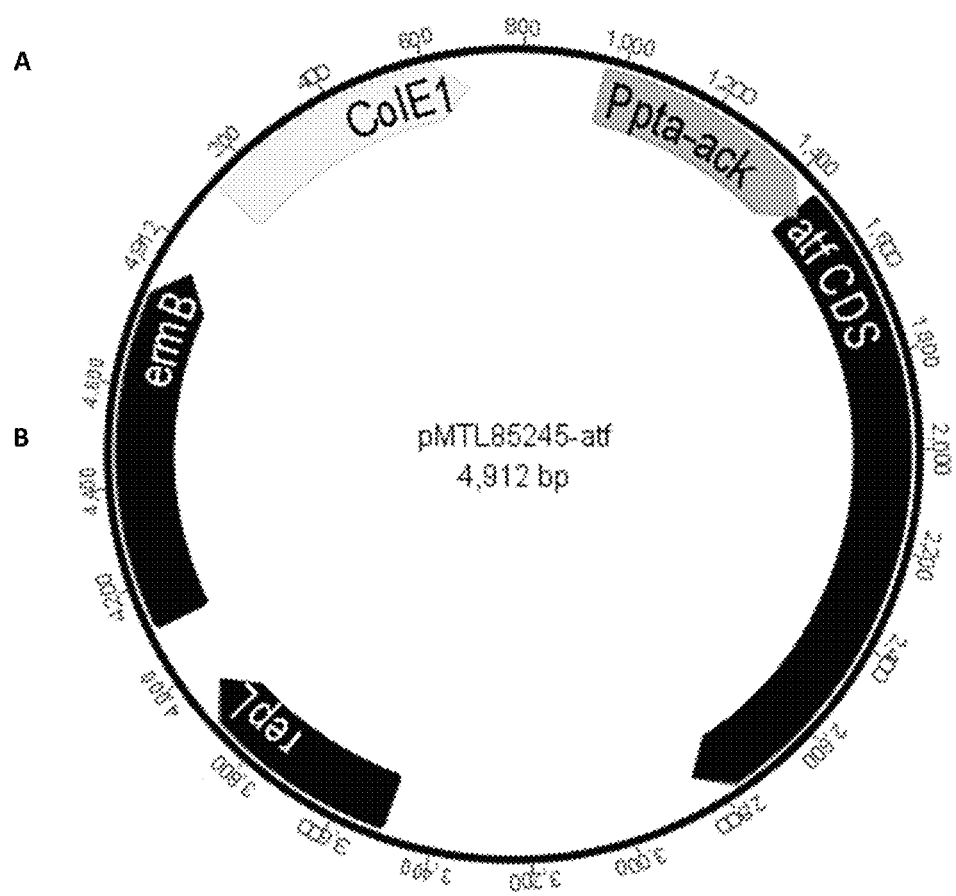
FIG. 2: Genetic map of expression plasmid pMTL85245-atf

The amplified 498 bp promoter region of the phosphotransacetylase/acetate kinase operon (Ppta-ack) was cloned into the *E. coli-Clostridium* shuttle vector pMTL 85241 (FJ797651.1; Nigel Minton, University of Nottingham; Heap et al., 2009) using NotI and NdeI restriction sites and strain DH5α-T1R (Invitrogen). Subsequently the synthesized acyl-transferase gene (SEQ ID NO: 1) was cloned in using NdeI and EcoRI to form plasmid pMTL85245-atf (SEQ ID NO: 5; FIG. 2). The insert was completely sequenced using oligonucleotides given in Table 2 and results confirmed that the atf gene was free of mutations.

TABLE 2

| Oligonucleotides for sequencing | | |
|---|---|---|
| Oligonucleotide Name | DNA Sequence (5' to 3') | SEQ ID NO: |
| Atf-F1 | AGACAACAACCTATGCATGTTGGAGGA | 6 |
| Atf-R1 | GGGGATGTGCTGCAAGGCGA | 7 |
| Atf-F2 | CATCATCAAGAAGGTTTGCAGCACAAT | 8 |
| Atf-R2 | AGAGGTTCTCTTGGACCTGGAACAT | 9 |
| Atf-F3 | TCGGTACCCGGGGATCCTCTA | 10 |
| Atf-R3 | CATTCCTGCTACTCCATCTACCATTGC | 11 |

Methylation of DNA:

Methylation of the FAEE expression plasmid pMTL85245-atf was performed in vivo in *E. coli* using a synthesized hybrid Type II methyltransferase (SEQ ID NO: 12) designed from methyltransferase genes from *C. autoethanogenum*, *C. ragsdalei* and *C. ljungdahlii*. The methyltransferase is fused to an inducible lac promoter (SEQ ID NO: 13) in vector pGS20 (SEQ ID NO: 14).

Both expression plasmid and methylation plasmid were transformed into same cells of restriction negative *E. coli* XL1-Blue MRF' Kan (Stratagene), which is possible due to their compatible Gram-(−) origins of replication (high copy ColE1 in expression plasmid and low copy p15A in methylation plasmid). In vivo methylation was induced by addition of 1 mM IPTG, and methylated plasmids were isolated using QIAGEN Plasmid Midi Kit (QIAGEN). The resulting mix was used for transformation experiments with *C. autoethanogenum* DSM23693, but only the abundant (high-copy) expression plasmid has a Gram-(+) replication origin (repL) allowing it to replicate in *Clostridia*.

Transformation into *C. autoethanogenum*:

During the complete transformation experiment, *C. autoethanogenum* DSM23693 was grown in PETC media (Tab. 1) supplemented with 1 g/L yeast extract and 10 g/l fructose as well as 30 psi steel mill waste gas (collected from New Zealand Steel site in Glenbrook, NZ; composition: 44% CO, 32% N2, 22% CO2, 2% H2) as carbon source.

To make competent cells, a 50 ml culture of *C. autoethanogenum* DSM23693 was subcultured to fresh media for 3 consecutive days. These cells were used to inoculate 50 ml PETC media containing 40 mM DL-threonine at an OD600 nm of 0.05. When the culture reached an OD600 nm of 0.4, the cells were transferred into an anaerobic chamber and harvested at 4,700×g and 4° C. The culture was twice washed with ice-cold electroporation buffer (270 mM sucrose, 1 mM MgCl$_2$, 7 mM sodium phosphate, pH 7.4) and finally suspended in a volume of 600 µA fresh electroporation buffer. This mixture was transferred into a pre-cooled electroporation cuvette with a 0.4 cm electrode gap containing 1 µg of the methylated plasmid mix and immediately pulsed using the Gene pulser Xcell electroporation system (Bio-Rad) with the following settings: 2.5 kV, 600Ω, and 25 µF. Time constants of 3.7-4.0 ms were achieved. The culture was transferred into 5 ml fresh media. Regeneration of the cells was monitored at a wavelength of 600 nm using a Spectronic Helios Epsilon Spectrophotometer (Thermo) equipped with a tube holder. After an initial drop in biomass, the cells started growing again. Once the biomass has doubled from that point, the cells were harvested, suspended in 200 µl fresh media and plated on selective PETC plates (containing 1.2% Bacto™ Agar (BD)) with 4 µg/ml Clarithromycin. After 4-5 days of inoculation with 30 psi steel mill gas at 37° C., colonies were visible.

The colonies were used to inoculate 2 ml PETC media containing 4 µg/µl Clarithromycin. When growth occurred, the culture was upscaled into 5 ml and later 50 ml PETC media containing 4 µg/ml Clarithromycin and 30 psi steel mill gas as sole carbon source.

Confirmation of the Successful Transformation:

To verify the DNA transfer, a plasmid mini prep was performed from 10 ml culture volume using Zyppy plasmid miniprep kit (Zymo). Since the quality of the isolated plasmid was not sufficient for a restriction digest due to Clostridial exonuclease activity [Burchhardt and Dürre, 1990], a PCR was performed with the isolated plasmid and oligonucleotides given in Table 2 to confirm the presence of the plasmid. PCR was carried out using iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes).

To confirm the identity of the clones, genomic DNA was isolated (see above) from 50 ml cultures of C. autoethanogenum DSM23693. A PCR was performed against the 16s rRNA gene using oligonucleotides fD1 (SEQ ID NO: 15: ccgaattcgtcgacaacAGAGTTTGATCCTGGCTCAG) and rP2 (SEQ ID NO: 16: cccgggatccaagcttACGGCTACCT-TGTTACGACTT) [Weisberg et al., 1991] and iNtRON Maximise Premix PCR kit (Intron Bio Technologies) with the following conditions: initial denaturation at 94° C. for 2 minutes, followed by 35 cycles of denaturation (94° C. for 20 seconds), annealing (55° C. for 20 seconds) and elongation (72° C. for 60 seconds), before a final extension step (72° C. for 5 minutes). Sequencing results were at least 99.9% identity against the 16s rRNA gene (rrsA) of C. autoethanogenum (Y18178, GI:7271109).

Growth Experiments to Confirm Biodiesel Production from CO:

To demonstrate FAEE production, PETC media were prepared and inoculated with C. autoethanogenum strain harboring expression plasmid pMTL85245-atf. Serum bottles with 50 mL PETC medium (Table 1) were pressurized with 30 psi of a CO containing gas stream from steel mill waste gas (collected from New Zealand Steel site in Glenbrook, NZ; composition: 44% CO, 32% N2, 22% CO2, 2% H2) and cultivated for 5 days. The same experiment was also carried out with the wild-type C. autoethanogenum strain without plasmid.

Figure 3:
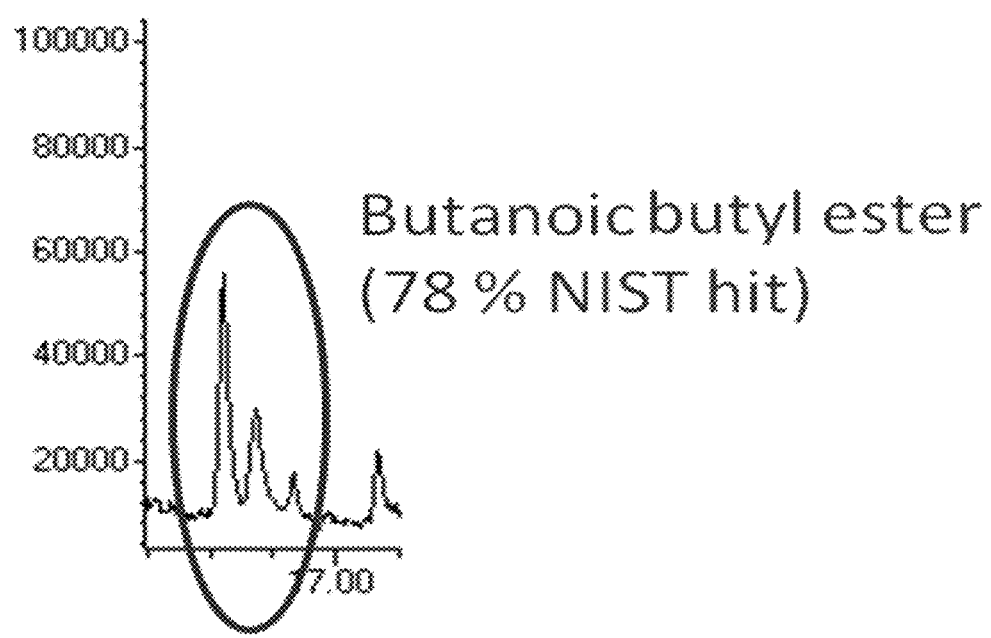
FIG. 3: GC-MS result confirming biodiesel production from CO.

The cultures were analyzed by GC-MS using headspace sampling. 2 mL sample in 20 mL vial were exposed for 10 min at 40° C. to a fibre (Supelco PDMS 100 fibre) and then analyzed using an Agilent 6890 GC with 5973 MSD equipped with a 30 m×0.25 mm×0.25 µm ZB-Wax column at following conditions: Injector temperature: 250° C.; Splitless injection; desorb for 10 min at 250° C.; 1 mL/min constant flow; Oven: 40° C. hold for 5 min, raise at 10° C./min to 190° C., hold for 5 min, raise at 3° C./min to 208° C., raise at 10° C./min to 220° C., hold 10 min, back to 40° C. at 60° C./min; MSD: Scan mode, mass range 38-650 AMU at 1.47 scans per second. Two peaks which matches to biodiesel substance butanoic acid butyl ester against the national Institute of Standards and Technology (NIST) standard reference database were found in the strain carrying the expression plasmid but not in the wild-type strain without plasmid, as well as some fatty acid products in C14-C18 range like 1-Octandecanol (C18) or Tetradecanal (C14), Heptadecane (C17), 9-Octadecanal (C18) and 11-Hexadecanal (C16) (Tab. 3; FIG. 3). Alcohols like ethanol and butanol were detected by HPLC performed using an Agilent 1100 Series HPLC system equipped with a RID operated at 35° C. (Refractive Index Detector) and an Aminex HPX-87H column (300×7.8 mm, particle size 9 µm) kept at 35° C. The RID was operated at 35° C. (Refractive Index Detector) and an Alltech IOA-2000 Organic acid column (150×6.5 mm, particle size 8 µm) kept at 60° C. Slightly acidified water was used (0.005 M $H_2SO_4$) as mobile phase with a flow rate of 0.25 ml/min. To remove proteins and other cell residues, 400 µl samples were mixed with 100 µl of a 2% (w/v) 5-Sulfosalicylic acid and centrifuged at 14,000×g for 3 min to separate precipitated residues. 10 µl of the supernatant were then injected into the HPLC for analyses.

TABLE 3

Results from GC-MS analysis of strain C. autoethanogenum harboring expression plasmid pMTL85245-atf:

| Retention Time | | % NIST match |
|---|---|---|
| 1.5-2.8 | $CO_2$ | 90 |
| 3.84 | Bisulfide | 90 |
| 4-4.5 | Acetic acid | 96 |
| 14.37 | 1-Octandecanol | <50 |
| 16.35 | Butanoic acid butylester | 50 |
| 16.64 | Butanoic acid butylester | 78 |
| 18.84 | Tetradecanal | 95 |
| 21 | Heptadecane | >90 |
| 21.7 | 9-Octadecanal(Z)/11-Hexadecanal(Z) | 93/87 |

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as an acknowledgment or any form of suggestion that they constitute valid prior art or form part of the common general knowledge in any country in the world.

Throughout this specification and any claims which follow, unless the context requires otherwise, the words "comprise," "comprising" and the like, are to be construed in an inclusive sense as opposed to an exclusive sense, that is to say, in the sense of "including, but not limited to."

REFERENCES

Abrini, J., Naveau, H., & Nyns, E. J. (1994). *Clostridium autoethanogenum*, sp. nov., an anaerobic bacterium that produces ethanol from carbon monoxide. *Archives of microbiology,* 161(4), 345-351.

Collins, M. D., Lawson, P. A., Willems, A., Cordoba, J. J., Fernandez-Garayzabal, J., Garcia, P., Cai, J., et al. (1994). The phylogeny of the genus *Clostridium*: proposal of five new genera and eleven new species combinations. *International journal of systematic bacteriology,* 44(4), 812-26.

Herbert, M., O'Keeffe, T. a., Purdy, D., Elmore, M., & Minton, N. P. (2003). Gene transfer into *Clostridium difficile* CD630 and characterisation of its methylase genes. *FEMS Microbiology Letters,* 229(1), 103-110.

Jennert, K. C., Tardif, C., Young, D. I., & Young, M. (2000). Gene transfer to *Clostridium* cellulolyticum ATCC 35319. *Microbiology* (Reading, England), 146 Pt 12, 3071-80.

Kita, A., Iwasaki, Y., Sakai, S., Okuto, S., Takaoka, K., Suzuki, T., Yano, S., et al. (2012). Development of genetic transformation and heterologous expression system in carboxydotrophic thermophilic acetogen *Moorella thermoacetica. Journal of Bioscience and Bioengineering,* xx(xx).

Köpke, M., Held, C., Hujer, S., Liesegang, H., Wiezer, A., Wollherr, A., Ehrenreich, A., et al. (2010). *Clostridium ljungdahlii* represents a microbial production platform based on syngas. *Proceedings of the National Academy of Sciences of the United States of America,* 107(29).

Köpke, M., Mihalcea, C., Liew, F., Tizard, J. H., Ali, M. S., Conolly, J. J., Al-Sinawi, B., et al. (2011). 2,3-Butanediol Production By Acetogenic Bacteria, an Alternative Route To Chemical Synthesis, Using Industrial Waste Gas. *Applied and environmental microbiology,* 77(15), 5467-75.

Leang, C., Ueki, T., Nevin, K. P., & Lovley, D. R. (2012). A Genetic System for *Clostridium ljungdahlii*: A Chassis for Autotrophic Production of Biocommodities and a Model Homoacetogen. *Applied and environmental microbiology,* (November).

Mermelstein, L. D., Welker, N. E., Bennett, G. N., & Papoutsakis, E. T. (1992). Expression of cloned homologous fermentative genes in *Clostridium acetobutylicum* ATCC 824. *Bio/technology (Nature Publishing Company),* 10(2), 190-195.

Perez, J. M., Richter, H., Loftus, S. E., & Angenent, L. T. (2012). Biocatalytic reduction of short-chain carboxylic acids into their corresponding alcohols with syngas fermentation. *Biotechnology and bioengineering,* 1-30.

Strätz, M., Sauer, U., Kuhn, a, & Dürre, P. (1994). Plasmid Transfer into the Homoacetogen *Acetobacterium woodii* by Electroporation and Conjugation. *Applied and environmental microbiology,* 60(3), 1033-7.

Tanner, R. S., Miller, L. M., & Yang, D. (1993). *Clostridium ljungdahlii* sp. nov., an acetogenic species in clostridial rRNA homology group I. *International journal of systematic bacteriology,* 43(2), 232.

Tyurin, Michael, & Kiriukhin, M. (2012). Electrofusion of cells of Acetogen *Clostridium* sp. MT 351 with erm (B) or cat in the chromosome. *Journal of Biotech,* 1-12.

Tyurin, M V, Desai, S., & Lynd, L. (2004). Electrotransformation of *Clostridium thermocellum. Applied and environmental mictrobiology* 70(2), 883-890.

Williams, D. R., Young, D. I., & Young, M. (1990). Conjugative plasmid transfer from *Escherichia coli* to *Clostridium acetobutylicum. Journal of general microbiology,* 136(5), 819-26.

We claim:

1. A genetically engineered carboxydotrophic acetogenic bacterium comprising an exogenous nucleic acid encoding an unspecific acetyltransferase comprising SEQ ID NO: 18.

2. The bacterium of claim 1, wherein the bacterium is a member of the genus *Clostridium*.

3. The bacterium of claim 1, wherein the unspecific acyltransferase is derived from *Acinetobacter baylyi*.

4. The bacterium of claim 1, wherein the bacterium is derived from *Clostridium autoethanogenum*.

5. The bacterium of claim 1, wherein the bacterium is derived from *Clostridium ljungdahlii*.

6. The bacterium of claim 1, wherein the bacterium is derived from *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Butyribacterium methylotrophicum, Acetobacterium woodii, Alkalibaculum bacchii, Blautia producta, Eubacterium limosum, Moorella thermoacetica, Moorella thermautotrophica, Sporomusa ovata, Sporomusa silvacetica, Sporomusa sphaeroides, Oxobacter pfennigii,* or *Thermoanaerobacter kiuvi*.

7. The bacterium of claim 1, wherein the bacterium produces biodiesel.

8. The bacterium of claim 7, wherein the biodiesel comprises fatty acid ethyl esters.

9. The bacterium of claim 1, wherein the bacterium converts a gaseous substrate comprising CO and/or $CO_2$ into biodiesel.

10. The bacterium of claim 7, wherein the biodiesel comprises fatty acid butyl esters.

11. The bacterium of claim 9, wherein the gaseous substrate comprises an industrial off or waste gas.

12. The bacterium of claim 9, wherein the gaseous substrate comprises syngas.

* * * * *